US006773877B2

(12) United States Patent
Fahy

(10) Patent No.: US 6,773,877 B2
(45) Date of Patent: Aug. 10, 2004

(54) METHODS OF USING ICE-CONTROLLING MOLECULES

(75) Inventor: Gregory M. Fahy, Riverside, CA (US)

(73) Assignee: Organ Recovery Systems, Inc., Charleston, SC (US)

( * ) Notice: Subject to any disclaimer, the term of this patent is extended or adjusted under 35 U.S.C. 154(b) by 0 days.

(21) Appl. No.: 08/943,147

(22) Filed: Oct. 3, 1997

(65) Prior Publication Data

US 2003/0111638 A1 Jun. 19, 2003

Related U.S. Application Data

(63) Continuation-in-part of application No. 08/485,185, filed on Jun. 7, 1996, now Pat. No. 6,303,388, which is a continuation-in-part of application No. 08/413,370, filed on Mar. 30, 1995, now abandoned.

(51) Int. Cl.$^7$ .............................. A01N 1/00; A01N 1/02; E01H 8/02; C09K 3/18
(52) U.S. Cl. ...................... 435/1.3; 244/134 R; 37/197; 252/70
(58) Field of Search .................... 435/1.3, 260; 252/70; 244/134 R; 37/197; 102/13

(56) References Cited

U.S. PATENT DOCUMENTS

| 4,484,409 A | 11/1984 | Caple et al. |
| 5,118,792 A | 6/1992 | Warren et al. |
| 5,174,498 A | 12/1992 | Popovitz-Biro et al. |
| 5,239,819 A | 8/1993 | Kinneberg |
| 5,251,398 A | 10/1993 | Balassa |
| 5,358,931 A | 10/1994 | Rubinsky et al. |

FOREIGN PATENT DOCUMENTS

| EP | 0 628 628 A1 | 12/1994 |
| WO | WO 94/24413 | 10/1994 |
| WO | WO 95/01606 | 1/1995 |
| WO | WO 96/30459 | 10/1996 |

OTHER PUBLICATIONS

Buerkle et al. "Cryopreservation of mouse oocytes by using DMSO and sucrose as cryoprotectants", Fertilitaet 4 (1) : 21–5 (1988).*
Webster's New World Dictionary, Third College Edition, p. 155, (1988).*
Dictionary of Microbiology and Molecular Biology, Second Edition eds. Singleton and Sainsbury, p. 715 (1994).*
Budavari, S., et al., Eds. The Merck Index, Eleventh Edition, Merck & Co., Inc., USA, 1989, Monograph 7073.*
O'Connell et al., Cryoprotectants for *Crithidia fasciculata* Stored at –20 C, with Notes on *Trypanosoma gambiense* and *T. conorhini*. The Journal of Protozoology 15(4):719–724, 1968.*

Sicheri, F. et al., "Ice–binding structure and mechanism of an antifreeze protein from winter flounder," *Nature*, vol. 375, 1995, pp. 427–431.
Wen, Dingyi et al., "Structure–Function Relationships in an Antifreeze Polypeptide," *The Journal of Biological Chemistry*, vol. 268, No. 22, 1993, pp. 16401–16405.
Chao, Heman et al., "Structure–function relationship in the globular type III antifreeze protein: Identification of a cluster of surface residues required for binding to ice," *Protein Science*, vol. 3, 1994, pp. 1760–1769.
Gordon, Eric M. et al., "Applications of Combinatorial Technologies to Drug Discovery. 2. Combinatorial Organic Synthesis, Library Screening Strategies, and Future Directions," *Journal of Medicinal Chemistry*, vol. 37, No. 10, 1994, pp. 1385–1401.
Powell, M. J. et al., "Catalytic antibodies—a new direction in enzyme design," *Protein Engineering*, vol. 3, No. 2, 1989, pp. 69–75.
Lerner, Richard A. et al., "Catalytic Antibodies," *Scientific American*, vol. 258, No. 3, 1988, pp. 42–50.
Lehn, Jean–Marie, Supramolecular Chemistry—Scope and Perspectives—Molecules, Supermolecules, and Molecular Devices (Nobel Lecture), *Angewandte Chemie*, vol. 27, No. 1, 1988, pp. 89–112.
Parody–Morreale, Antonio et al., "Inhibition of bacterial ice nucleators by fish antifreeze glycoproteins," *Nature*, vol. 333, 1988, p. 782.
Chemical Abstracts, vol. 105, No. 3, Jul. 21, 1986, Columbus, Ohio, US; Abstract No. 23626.
Chemical Abstracts, vol. 70, No. 23, Jun. 9, 1969, Columbus, Ohio, US; Abstract No. 103995.
P. L. Davies et al., "Biochemistry of Fish Antifreeze Proteins", *The FASEB Journal*, vol. 4, May 1990, pp. 2460–2468.
D. S. Yang et al., "Crystal Structure of an Antifreeze Polypeptide and its Mechanistic Implications", *Nature*, vol. 333, May 19, 1988, pp. 232–237.

(List continued on next page.)

*Primary Examiner*—Sandra E. Saucier
(74) *Attorney, Agent, or Firm*—Oliff & Berridge, PLC

(57) ABSTRACT

A dispersal pattern of hydrogen bonding sites on an ice surface is used as a template in a process for the design, selection and manufacture of synthetic ice interface dopants. Ice interface dopants are generally molecules which bind to a surface of an ice crystal and inhibit subsequent gain or loss of water molecules. The ice interface dopants can thus inhibit ice crystal growth, recrystallization, and sublimation. Ice interface dopants can also inhibit heterogeneous nucleating agents, and thus postpone or prevent ice nucleation. On the other hand, very strong IIDs may be used as well to beneficially induce ice nucleation. Exemplary dopant structures are provided that achieve near-perfect ice-bonding efficiency while being thoroughly adaptable to a wide variety of specialized ice-bonding applications. Orbital steering provides for steering lone pair orbitals of ice bonding atoms in the interface dopant to result in an optimal angular alignment with the complementary binding sites on ice.

5 Claims, 25 Drawing Sheets

OTHER PUBLICATIONS

K. Chou, "Energy-optimized Structure of Antifreeze Protein and its Binding Mechanism", *J. Mol. Biol.*, vol. 223, 1992, pp. 509–517.

M. Gavish et al., "Ice Nucleation by Alcohols Arranged in Monolayers at the Surface of Water Drops", *Science*, vol. 250, Nov. 16, 1990, pp. 973–975.

M. Gavish et al., "The Role of Crystal Polarity in α–Amino Acid Crystals for Induced Nucleation of Ice", *Science*, vol. 256, May 8, 1992, pp. 815–818.

C. Knight et al., "Fish Antifreeze Protein and the Freezing and Recrystallization of Ice", *Nature*, vol. 308, Mar. 15, 1984, pp. 295–296.

A. DeVries, "Biological Antifreeze Agents in Coldwater Fishes", *Comp. Biochem. Physiol.*, vol. 73A, No. 4, 1982, pp. 627–640.

G.M. Fahy et al., Abstract No. 213, *Cryobiology*, 28, 584, 1991.

F. Franks et al., "Blood Glycoprotein from Antarctic Fish Possible Conformational Origin of Antifreeze Activity", *Biochimica et Biophysica Acta*, vol. 540, 1978, pp. 346–356.

R. Pain, "Helices of Antifreeze", *Nature*, vol. 333, May 19, 1988, pp. 207–208.

C. Knight et al., "Adsorption to Ice of Fish Antifreeze Glycopeptides 7 and 8", *Biophys. J. Biophysical Society*, vol. 64, Jan. 1993, pp. 252–259.

C. Knight et al., "Adsorption of α–Helical Antifreeze Peptides on Specific Ice Crystal Surface Planes", *Biophysical Journal*, vol. 59, Feb. 1991, pp. 409–418.

D. Wen et al., "A Model for Binding of an Antifreeze Polypeptide to Ice", *Biophys. J. Biophysical Society*, vol. 63, Dec. 1992, pp. 1659–1662.

A. DeVries, "Role of Glycopeptides and Peptides in Inhibition of Crystallization of Water in Polar Fishes", *Phil. Trans. R. Soc. Lond.*, vol. B 304, 1984, pp. 575–588.

J. Raymond et al., "Adsorption Inhibition as a Mechanism of Freezing Resistance in Polar Fishes", *Proc. Natl. Acad. Sci. USA*, vol. 74, No. 6, Jun. 1977, pp. 2589–2593.

Z. Yosida, "Surface Structure of Ice Crystal and its Equilibrium Form", *Cellular Injury and Resistance in Freezing Organisms*, International Conference on Low Temperature Science, I., Conference on Physics of Snow and Ice (*E. Asahina*, ed.), The Institute of Low Temperature Science, Sappora, Japan, 1967, p. 2 and 10–11.

F. Franks, "The Physics of Water at Subzero Temperatures", *Biophysics and Biochemistry at Low Temperatures*, Cambridge University Press, New York 1985, p. 21.

E. Whalley, "Structure Problems of Ice", *Physics of Ice Proceedings of the International Symposium on Physics of Ice*, Munich, Germany, Sep. 9–14, 1968 N. Riehl, B. Bullemer, and H. Engelhardt, eds., 1969, pp. 21–33.

D. Wu et al., "Activation of Antifreeze Proteins from Larvae of the Beetle Dendroides Canadensis", *J. Comp. Physiol B.*, vol. 161, 1991, pp. 279–283.

J. T. Eastman et al., "Antarctic Fishes", *Scientific American*, vol. 254, Nov. 1986, pp. 106–114.

J. Madura et al, "Interactions of the D– and L–Forms of Winter Flounder Antifreeze Peptide with the (201) Planes of Ice", *J. Am. Chem. Soc.*, vol. 116, No. 1, 1994, pp. 417–418.

G. Fahy, "The Role of Nucleation in Cryopreservation", *Biological Ice Nucleation and Its Applications*, Chapter 18, pp. 315–336, 1995.

A. Parody–Morreale et al., "Inhibition of Bacterial Ice Nucleators by Fish Antifreeze Glycoproteins", *Nature*, vol. 333, No. 6175, pp. 782–783, Jun. 1988.

F. Sicheri et al., "Ice–binding Structure and Mechanism of an Antifreeze Protein From Winter Flounder", *Nature*, vol. 375, pp. 427–431, Jun. 1995.

Aspen Systems, Inc., "Aircraft De–icing Agent", http://www.aspensystems.com/deicer.html, 1996.

Allen, William, "William Welsh is Fighting Ice with Fire Beetles", *St. Louis Post–Dispatch*, Sep. 6, 1994, News Section, p. 1B.

Kiel, Jacqueline, "Freezing Avoidance in Antarctic Fishes (S–005M)", *Antarctica Sun Times–Online*, Nov. 10, 1996, http://www.asa.org/nsfa/astnov10.htm.

MDL Information Systems, Inc., "Combinatorial Chemistry: A Strategy for the Future", Mar. 1995, *Molecular Connection*, 1997, http://www.mdli.com/info/comchem.html.

Jia Zongchao et al., "Structural basis for the binding of a globular antifreeze protein to ice," *Nature*, vol. 384; Nov. 21, 1996, pp. 285–288.

Rubinsky et al., Hypothermic Protection–A fundamental property of "Antifreeze" proteins, *Biochemical and Biophysical Research Communications*, 1991, vol. 180(2), pp. 566–571.

Kao et al., "The Relationship between molecular weight and antifreeze polypeptide activity in marine fish", Can., J. Zool, 1986, vol. 64, pp. 5788–582.

Wu et al., "Enhancement of insect antifreeze protein activity by antibodies", *Biochema et Biophysica Acta.*, 1991, vol. 1076(3), pp. 416–420.

J.D. Schrag et al., "Primary and Secondary Structure of Antifreeze Peptides from Arctic and Antarctic Zoarcid Fishes", *Biochimica et Biophysica Acta*, vol. 915, pp. 357–370, 1987.

R. Evans, "An Introduction to Crystal Chemistry Second Edition", pp. 266–271 (1964).

Welsh, William J., http://macross.uml.edu/umsl_chem/faculty/William.J. Welsh.html (1997).

Cloud, Aerosol, and Precipitation Physics and Chemistry, "Fundamental Physics of Ice Formation", http://www.ncar.ucar.edu/archives/ asr/ASR94/MMM/capchem.html (1994).

Terrett, Nick, "Combinatorial Chemistry", *Tetnet–The electronic version of Tetrahedron News*, http://oxford.elsevier.com/tis/tetnet/tetnet 1.htm (1996).

V. J. Hruby, "Conformational and Topographical Considerations in the Design of Biological Active Peptides", *Biopolymers*, vol. 33, pp. 1073–1082 (1993).

Gupta et al., "Importance of van der Waals Volume n QSAR Studies for Drugs". *Journal of Scientific and Industrial Research*, vol. 44, pp. 189–198 (1985).

P. Dean, "Recent Advances in Drug Design Methods: Where Will They Lead", *BioEssays*, vol. 16(9), pp. 683–687 (1994).

G.J. Moore, "Designing peptide mimetics", *TIPS*, vol. 15, pp. 124–129 (1994).

\* cited by examiner

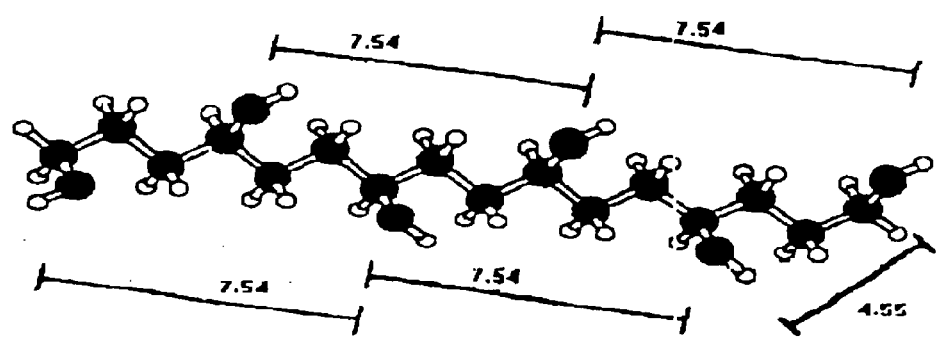

METHODS OF USING ICE-CONTROLLING MOLECULES

This application is a Continuation-In-Part application of U.S. patent application Ser. No. 08/413,370, filed Mar. 30, 1995, now abandoned, and Ser. No. 08/485,185, filed Jun. 7, 1996, now U.S. Pat. No. 6,303,388, which is a continuation-in-part of U.S. patent application Ser. No. 08/413,370, filed Mar. 30, 1995, the entire texts of which are hereby incorporated by reference.

BACKGROUND OF THE INVENTION

Ice formation is damaging to living systems and food products and may be a nuisance and a hazard to human beings who must cope with snow and ice in their environment. The field of the present invention is the provision of processes for the preparation of specific chemical agents, referred to herein as ice interface dopants (IID), that will effectively reduce ice formation and make ice that does form innocuous to living systems and foodstuffs and less troublesome and hazardous to humans and machinery in the environment.

Referring to FIGS. 1A–1B, ice crystallizes in the shape of a hexagonal plate 10. A plane defined by the a axis 12 and the b axis 14 (which is crystallographically identical to the a axis) and perpendicular to the c axis 16 defines a hexagonal cross section called the basal plane 18. The six faces of the hexagon are called prism faces 20. Crystallographically, the basal plane 18 is referred to as the 0001 surface, and the prism face is referred to as the $1\bar{1}00$ surface or the $1\bar{1}20$ surface depending on the orientation.

FIGS. 2A–2D show that the units of the crystal that give rise to this macroscopic structure are also hexagonal. In FIG. 2A, following common usage, only the oxygen atoms are represented. Stippling indicates oxygens projecting out of the plane of the sheet. The hydrogen atoms lie along the straight lines shown bonding each oxygen atom to its four nearest neighbors.

FIG. 2A shows the basal plane 0001 surface as seen from above. Within each hexagon, three vertices project upward (or forward), and the three intervening vertices project downward (or backward). The upward vertices are separated by 4.5 Å±0.02 Å and are located at a 60° angle with respect to each other. Their fourth bonds extend perpendicularly out of the page toward the viewer. Another spacing at 7.36 Å separates alternate bilayers 21 of oxygen atoms in the lattice, or, viewed differently, separates each oxygen-defined hexagon from an identical hexagon located immediately adjacent to it. FIG. 2B shows a perspective view of the prism face. Crystallographically, the prism face may be represented as the $c1\bar{1}00$ (FIG. 2C) or $d11\bar{2}0$ (FIG. 2D) prism faces, depending on the angle of the viewer.

Several natural molecules exist that alter the behavior of ice and of water. Antifreeze glycoproteins (AFGPs) and antifreeze proteins or antifreeze peptides (AFPs) produced by several species of fish are believed to adsorb preferentially to the prism face 20 of ice and thus to inhibit ice crystal growth perpendicular to the prism face, i.e, in the direction extending along the basal plane 18 and along the a and b axes 12 and 14.

This capability is sufficient to permit certain fish to live their entire lives at a body temperature about 1° C. below the thermodynamic freezing point of the fishes' body fluids. These fish can ingest and contact ice crystals that might otherwise provide crystal nucleation sites without being invaded by the growth of ice through their supercooled tissues because the AFGPs present in their tissues and body fluids block ice growth despite the presence of supercooling. Insect antifreeze or "thermal hysteresis" proteins (THPs) are even more effective, being active at supercooling levels of 2° C. or more below the thermodynamic freezing point.

The natural "antifreeze" or "thermal hysteresis" proteins found in polar fish and certain terrestrial insects are believed to adsorb to ice by lattice matching (Davies and Hew, *FASEB J.*, 4; 2460–2468, 1990) or by dipolar interactions along certain axes (Yang, Sax, Chakrabartty and Hew, *Nature*, 333:232–237, 1988).

AFGPs and AFPs found in certain organisms provide natural "proofs of principle" for the concept of novel man-made IIDs. However, natural ice interface doping proteins are not sufficiently active or abundant for most practical applications of interest. Furthermore, a disadvantage of growth inhibition on the prism faces is that, when supercooling becomes sufficient to overcome ice crystal growth inhibition, growth occurs, by default, predominantly in the direction of the c axis 16, perpendicular to the basal plane 18. This results in the formation of spicular or needle-shaped ice crystals (FIG. 1B) that are more damaging to living cells than normal ice, apparently for mechanical reasons. (In FIG. 1B, AFGPs are represented as blobs blocking the prism faces. Other layers are similarly blocked, but the details are omitted for simplicity.)

Natural IIDs are commercially available only in a very limited quantity and variety. Furthermore, they must have fairly high relative molecular masses (typically at least about 4,000 daltons) to be effective. This tends to make them expensive, and they often require complex interactions with other hard-to-acquire proteins and often require carbohydrate moieties for full effectiveness. Insect antifreeze proteins, recently shown to be extremely effective compared to fish antifreeze proteins, still have relative molecular masses of around 8,400 daltons. (Graham, Liou, Walker and Davies, *Nature*, 388:727–728, 1997).

Furthermore, addition of natural fish AFGP to a concentrated solution of cryoprotectant (30–40% v/v DMSO) had minimal effect on ice crystal growth rates below −20 to −40° C. (Fahy, G. M., in *Biological Ice Nucleation and its Applications*, chapter 18, pp. 315–336, 1995), thus making questionable its effectiveness for use in organ vitrification for cryopreservation.

Another problem with natural antifreeze proteins is that continuing confusion over their precise mechanisms of action hampers the development of recombinant variants that could be more effective. Recently, Warren and colleagues reported some progress in this direction (U.S. Pat. No. 5,118,792).

Caple et al. (*Cryo-Letters*, 4:51–58, 1983) made several apparently arbitrary synthetic polymers and showed that some of them were able to prevent nucleation of water by silver iodide crystals. They suggested that these polymers adsorbed either to the silver iodide or to ice crystal nuclei, but they did not suggest any specific interactions, and their polymers were made without regard to any consideration of the structure of ice or of AgI. Further, except for noting that a 2 to 1 ratio of hydrophobic to hydrophillic groups on their polymers gave maximum inhibition of nucleation, they provided no guidance or general principles as to how one could approach the synthesis of ice-binding polymers on a systematic theoretical or empirical basis or maximize the ice-binding effectiveness of such polymers. They also taught that higher concentrations of their polymers nucleated their solutions, and failed to teach that their polymers would slow ice crystal growth rates or have other than academic uses. Caple et al. (*Cryo-Letters,* 4: 59–64, 1983) also reported detecting unidentified, uncharacterized, and unpurified nucleation-inhibiting substances from natural sources, but again suggested no applications.

The concept of designing specific artificial chemical agents whose purpose is to control the physics of ice was first mentioned by Fahy in *Low Temperature Biotechnology*, McGrath and Diller, eds., ASME, pp.113–146, 1988. The sole mention of this idea was the single statement that "insight into the mechanism of AFP action . . . opens the possibility of designing molecules which may be able to inhibit ice crystal growth in complementary ways, e.g., along different crystallographic planes." However, no method of preparing such molecules was suggested.

Kuo-Chen Chou ("Energy-optimized structure of antifreeze protein and its binding mechanism", *J. Mol. Biol.,* 223:509–517, 1992) mentions an intention to specifically design ice crystal growth inhibitors. However, it is confined to minor modifications of existing antifreeze molecules, and does not envision the present radically different approach of preparing synthetic IIDs de novo.

Based on these observations, it is advantageous to design molecules that can inhibit ice crystal growth specifically in the direction of the c axis in accordance with the present invention. When used in combination with an agent acting to block growth in the direction of the basal plane, such that all growth planes would be inhibited rather than only one, such an agent should avoid the lethal drawbacks of the prior art of freezing cells using only basal plane growth inhibitors. Furthermore, since growth in the direction of the c axis, hereinafter "C growth," is the limiting factor for supercooling in the presence of agents that adsorb to the prism face (agents that block growth in the a axis direction, or "A growth"), C growth inhibitors should enhance supercooling considerably over the supercooling achievable with A growth inhibitors alone when used in combination with A growth inhibitors.

A problem with natural antifreeze proteins has been continuing confusion over their precise mechanisms of action. Recently, Sicheri and Yang (*Nature,* 375:427–431, 1995) described a clear model of how AFPs undergo lattice matching with ice. They indicated that, of 8 AFPs examined, the number of ice-binding atoms ranged from 3 to 10 per AFP and that each AFP formed, on average, ice contacts at between 1 in every 4.8 to 1 in every 15 amino acids present in the molecule (roughly 1 ice bond per 422–1340 daltons of AFP mass). The ice-binding amino acids were threonine (thr), aspartate (asp), asparagine (asn), and lysine (lys). Each binding amino acid formed one bond per amino acid and the bonds were formed by the hydroxyl oxygen of thr, the amino nitrogen of lys and of asn, and the acid oxygen ($O^-$ or carbonyl O) of asp. For the winter flounder AFP, detailed analysis showed that the lattice matching depended on a planar arrangement of the AFP's bonding groups and on geometrical constraints on the freedom of motion of the matching groups. Bonding took place on the ridges of the 2021 plane (*Biophys. J.,* 63:1659–1662, 1992; *Faraday Discuss.,* 95:299–306, 1993; *J. Am. Chem. Soc.,* 116:417–418, 1994.) More detailed analysis showed that the lattice match between asn and asp oxygen and nitrogen and ice oxygens was imperfect. For one thing, the oxygens in ice associated with these sites were located to the side of each binding atom, not directly underneath. For another, the trigonal planar (sp2) coordination of the hydrogen-bonding groups of asn and asp differ from the tetrahedral (sp3) coordination of oxygens in ice. They concluded that "the underlying hydrogen-bonding interactions are likely to be more liberally defined than previously proposed" by other authors (*Biophys. J.,* 59: 409–418, 1991; *Biophys. J.,* 63:1659–1662, 1992; *Biophys. J.,* 64: 252–259, 1993).

SUMMARY OF THE INVENTION

The present invention provides processes for preparing ice interface dopants, ice interface dopants prepared thereby, and methods of using them. One process entails determining a distance between hydrogen bonding sites on an ice nucleating substance and preparing molecules having a complementary bonding distance between their own hydrogen bonding sites and the identified sites on the ice nucleating substance. Enhanced ice bonding capacity of these molecules is obtained by considering in a design process the novel concept of "orbital steering." Orbital steering refers to the positioning of lone pair electron orbitals (or hydrogen atoms capable of forming hydrogen bonds) in a preferred direction so as to facilitate hydrogen bonding to ice. This may be accomplished by locking the bonding atoms of the IID into fixed, non-rotating positions by covalently bonding them to at least two other atoms other than hydrogen that form a part of the relatively rigid structure of the IID. Alternately, orbital steering can be accomplished using only rotatable ice-bonding groups whose ice-bonding orbitals are designed to be able to aim directly at hydrogen bonding orbitals of ice. Molecules of the invention may be designed in such a way that they can be both highly active and sufficiently available to be practical to use.

According to the present invention, IIDs can be prepared that exceed the effectiveness of natural agents. Given that nature has been constrained to using protein, which has limited chemical and structural versatility, and limited evolutionary flexibility, non-protein IIDs as provided herein can vastly exceed the performance of existing natural antifreeze macromolecules, provided proper procedures, as provided by the present invention, are followed. By analogy, the fact that insect AFPs are many times more active than fish proteins shows that the principles used by fish proteins can be improved upon. Synthetic IIDs should exceed insect AFP effectiveness by using principles superior to those used by the insect proteins. The present invention provides methods of preparing new and optimal non-protein structures for inhibiting ice crystal formation without regard to existing natural antifreeze proteins or glycoproteins.

The dopant molecules of the present invention can be prepared to adsorb to each surface facet ice presents. Dopant molecules can be prepared to act cooperatively by providing binding sites for other dopant molecules along the edges of the molecule. The invention provides processes for the preparation of molecules that can effectively adsorb to an ice lattice or another ice nucleating surface to preclude ice crystal growth at these ice nucleating surfaces. Additionally, the invention provides processes for the preparation of molecules that can cause nucleation.

The present invention also provides methods for inhibiting the growth of ice in and on various objects, for example, aircraft wings, footwear, pathways, foodstuffs, plants, windows, cables, transplantable organs, tissue, or cells including blood tissues or cells, and other substances or objects where control of ice growth is beneficial.

A process embodied in the invention includes a process for preparing an ice interface dopant comprising determining at least one distance between a plurality of ice crystal template hydrogen bonding sites on a substance capable of nucleating an ice crystal and synthesizing a dopant molecule having a plurality of dopant hydrogen bonding sites spaced at such a distance as to be capable of associating simultaneously with said ice nucleating substance hydrogen bonding sites.

Embodiments also include determining said distance by binding at least one polymer to said ice nucleating substance hydrogen bonding sites, said polymer comprising a polynucleotide that is capable of being amplified directly or indirectly by PCR.

Most particularly, the present invention relates to motifs for ice bonding that allow a) positional matching between hydrogen bonding atoms in ice and of ice-bonding atoms in the IID, b) orbital positioning of those bonding atoms for bonding to hydrogen bonding sites in ice, c) versatility to permit any matching region of ice vertices to be bonded, regardless of whether the locally available ice vertices are projecting hydrogen atoms or oxygen lone pair electron clouds toward the IID, and d) polymerization to form chains that will provide IIDs of desired effectiveness.

BRIEF DESCRIPTION OF THE DRAWINGS

FIG. 5A presents a view looking down on the basal plane of an ice crystal; FIG. 5B shows the complex rotated to clearly show hydrogen bonding between the ice and dopant molecule; and FIG. 5C shows the dopant with only the water molecules of the upper layer of the ice lattice structure.

FIGS. 19A and 19B show the match between a linear IID and the surface topography of the basal plane of ice. (FIG. 19B shows that hydroxyls can match an ice lattice when properly stereospecifically placed in a linear chain, and spaced by a correct number of carbon atoms.)

DETAILED DESCRIPTION OF PREFERRED EMBODIMENTS

Figure 1A:
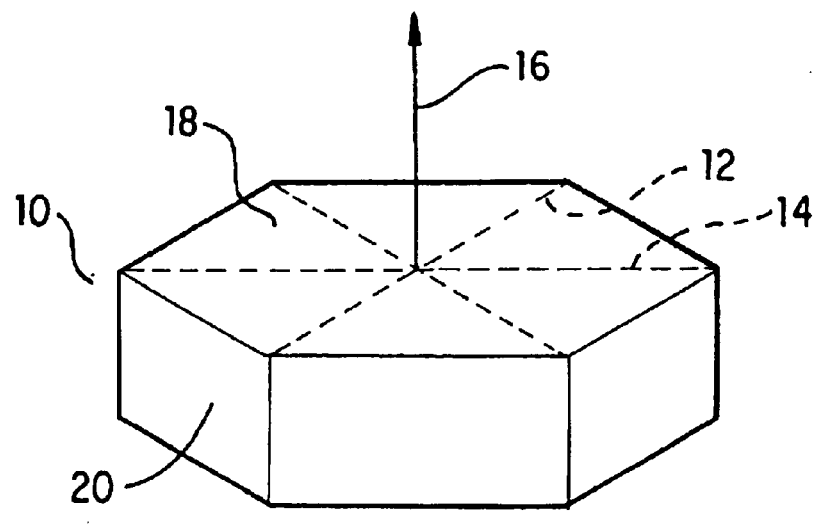
FIG. 1A shows the macroscopic prism structure of an ice crystal, including the surface arrangement of the basal plane and the prism faces.

The principles described herein permit IIDs to be designed to bind to any crystallographic plane of ice desired whatever, or even to non-crystallographic patterns inherent in the ice crystal structure. Specific molecular prototypes described herein have been designed specifically to bind to the basal plane so as to prevent C growth, but these specific prototypes are to be understood to be illustrative, not limiting.

Although the details of preparation of different IID classes as described herein will differ somewhat depending on the specific application, the following primary criteria apply in varying degrees to all categories.

An ice interface as defined herein is the portion of a surface capable of nucleating ice crystal growth. An ice crystal presents several such surfaces and is used throughout the specification as an exemplary ice interface. Heterogeneous nucleators are also considered to possess ice interfaces that may be blocked by the molecules of the instant invention.

The preparation of IIDs by any of the following criteria or combinations thereof will be significantly facilitated by use of adequate computational chemistry packages. Suitable packages include "HyperChem" and "Hyperchem Lite", "ECEPP/2" (see Chou, *J. Mol. Biol.*, 223:509–517, 1992), and "Insight II, Discover, and Analysis" (made by Biosim Technologies, Incorporated, Parsippany, N.J.), or the direct programs upon which they are based, such as "MM2" (Dr. Norman Allinger, University of Georgia). Many less rigorous but still useful programs can also be used. All of these programs are hereby incorporated by reference.

Physical molecular models can also be used to suggest computational molecular models. Physical molecular models allow one to rapidly get a feel for atomic arrangements that accomplish the desired objectives, and they allow for easy visualization of lone pair electron positions in ways not always available using computational models. This is critical because it is often lone pair electrons that bind to hydrogen atoms in the ice crystal lattice.

The following considerations define criteria used for the design and preparation of the various IID molecules:

a. Principles for Balancing the Conflicting Considerations of Molecular Mass, Molecular Mobility, and Molecular Bonding to Ice. The water molecule is only 18 daltons in mass, and is thus highly mobile in comparison with any structure that may be synthesized for the purpose of inhibiting water adsorption to an existing ice crystal. For the IID to compete maximally with water for access to the advancing ice interface, the molecular mass of the IID should be kept to a minimum. This is particularly true for fast cooling situations. Furthermore, the cost of synthesizing artificial molecules generally goes up as the mass of the molecules becomes larger. Thus, the mass of synthetic IIDs of the present invention is preferably maintained at or under 4500 daltons, and more preferably at or under about 1000–3000 daltons. As disclosed herein, IIDs can be designed with a molecular mass as low as about 100–500 daltons.

By the same token, the effectiveness of a given IID molecule will depend on the area of the ice nucleating interface, for example an ice crystal, that it can cover and on the number of bonds it can form with the ice interface, and both of these will generally decrease as its molecular mass decreases. These factors presumably explain in part why effective natural AFPs are several thousand daltons in mass. Furthermore, excessive molecular mobility on the part of synthetic IIDs could allow high rates of detachment from the ice interface in addition to high rates of attachment to the ice interface.

Yet another factor that will make low mass adverse in some (e.g., biological) though not in other (e.g., industrial) IID applications is the higher osmotic effect of low-mass molecules per unit weight.

To offset the negative effects of lower molecular mass, each IID should satisfy the following criteria.

1. Synthetic IIDs should exceed natural IIDs' ratio of ice bonds to IID mass. According to Chou (J. Mol. Biol., 223:509–517, 1992), the 37 amino acid flounder antifreeze protein forms one bond to ice at every eleventh amino acid. This results in a total of four ice bonds per molecule, or one ice bond for every 819 daltons. Synthetic IIDs should possess a bond to mass ratio of approximately 1 bond per 50 to 500 daltons. Bonding sites should be linearly disposed, that is essentially one dimensional, to minimize nucleation tendency. Alternatively, the ice bonding portion of the molecule should be of limited width or local area for the same reason. Lattice matching over large contiguous areas promotes nucleation (Gavish et al., Science, 250:973–975, 1990), but this tendency can be reduced or eliminated by spreading the matching sites apart and/or arranging them in lines.

2. The bonds formed by synthetic IIDs should be at least as strong as bonds formed by natural IIDs, and preferably stronger when nucleation tendencies can be avoided, such as by constructing an essentially linear molecule. Charged groups such as protonated amines or ionized oxygen (as in carboxylic and other acid groups) are preferred, both for strong hydrogen bonding to specific ice lattice sites and for breakdown of local water structure into a non-ice-like form, further discouraging crystal growth. Double-bonded oxygen in carbonyl, sulfoxide, sulfate and phosphate groups is also favored.

The upper limit to bond strength will be determined by chemical toxicity of the bonding group for applications where toxicity is a concern, by the compatibility of the geometry of strong bonding groups in the IID with the geometrical constraints of ice, by unfavorable attraction or repulsion between IIDs at these strongly ice-bonding sites, and by the tendency of particularly strong ice-binding sites to serve as nucleation sites. In certain embodiments, however, the nucleating tendency of very strong ice-bonding sites is not a disadvantage. For example, the preparation of low molecular mass, biodegradable organic nucleators would be of commercial value. Further, nucleator tendency can be an advantage if, at the same time the agent nucleates ice, it also adsorbs to the ice surface to prevent further growth.

3. A good way to form strong bonding without using exotic chemical groups is to rely on the principle of molecular recognition as exemplified, for example, by enzyme-substrate or hormone-receptor affinities. This involves, generally, a 3-dimensional fit between the feature being recognized and the recognizing molecule. Thus, the operating reference (or monomeric) mass of the IID is often preferably the minimum mass consistent with specific recognition of a particular feature of the ice crystal surface. Total mass may be one or more multiples of this operating reference mass.

Structure 1

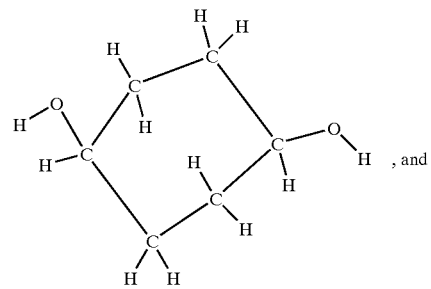

, and

Structure 2

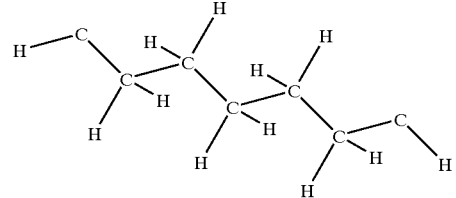

Sample structures 1 and 2 depict weak (low operating reference mass and therefore low bond number, plus minimal 3-dimensional character) ice recognition molecules with an operating reference mass of approximately 100 daltons (116 and 104 daltons, for structures 1 and 2 respectively). Since each structure has two ice-bonds, the mass to bond ratios are 58 and 52 daltons/bond respectively, compared to 819 for the flounder antifreeze protein.

In structure 1, oxygens are separated by 4.5 Å, and in structure 2 they are separated by precisely 7.36 Å, an amazingly exact fit to the ice lattice spacing in both cases.

4. Low atomic number atoms, such as boron and nitrogen, may be used to minimize IID molecular mass and thus maximize mobility and maximize the ratio of ice bonds to IID mass.

b1. Cooperativity and self-assembly. Cooperativity of bonding to ice inherent in a repeating polymer has the great advantage of summing ice interactions over large numbers of monomers, maximizing the number of bonds per molecule. An important principle allowing molecules to attain the economies of synthesis and high mobilities associated with lower molecular masses while at the same time attaining the major advantages of such cooperative binding is to design IIDs to serve as modules in a larger structure. Two examples are a) modules that are independent self-assembling molecules and b) modules that form monomers within a single polymeric molecule.

For separate molecular modules, side-to-side bonding between edges of the modules, such as hydrogen bonding, can occur when the modules are properly oriented to cooperatively interact with ice. This allows the modules as a population to rapidly self-assemble into an ice-covering surface when an invading ice front becomes available as a template to catalyze this self-assembly process. The mobility of each module allows the module with the most favorable orientation with respect to the intruding ice front to orient itself in the proper manner on the ice front. This slows the growth of the ice front while recruiting other monomers via side-to-side bonding to form an ice-covering film (an "induced fit" process). Laterally-assembling (parallel) rods or strips can form tighter bonds to the ice crystal surface overall than unassociated structures.

An example of a useful type of molecular self-assembly is provided by Ghadiri et al. ("Self-assembling organic nanotubes based on a cyclic peptide architecture", Nature, 366:324–327, 1993, hereby totally incorporated by reference). Ghadiri et al. discloses design of planar cyclic polypeptides that form hydrogen bonds to identical cyclic polypeptides above and below their own plane so as to generate long, self-assembling molecular tubes. The tubes in turn are associated side-to-side to generate structured 3-dimensional arrays. This work involved no recognition of any target molecules other than the cyclic polypeptides. Forming thick 3-dimensional structures is inappropriate for IIDS, which should form more-or-less 2-dimensional or cup-shaped or stair-stepped structures (to follow ice surface features and thereby maximize the ratio of IID-ice bonds to adsorbed IID mass). However, an essentially 2-dimensional analog of this work, with the further modifications indicated below, would be appropriate for IID preparation.

This approach is preferred in situations where a) there is no limitation on the amount of IID available to cover the ice surface (since this geometry could, by covering the ice surface too intensively at one site, deplete the supply of IID and therefore leave other ice faces uninhibited), and/or b) the IIDs are sufficiently well spaced (form "carpets" of limited extent) to avoid the development of nucleator activity that might arise from the IID organizing water molecules into an extensive planar ice-like structure, or c) nucleation is not undesirable or relevant.

b2. Synthesis of regular (periodic) polymers. The second modularity approach is modularity within a given molecule. When IIDs must be relatively large, it is generally more economical to create them if they can be designed as polymerization products of commonly-available smaller monomers. For example, glycogen is a polymerization product formed by condensation of glucose. A modified glucose molecule can be condensed into an IID of arbitrary molecular mass. Natural or modified nucleic acids and natural or modified amino acids can also be polymerized into IIDs of unlimited size at relatively low cost.

The IID should be designed to prevent self-association at its ice-bonding side, and preferably also at its complementary side facing away from the ice front. Mutual association of ice-bonding sides will block the functional, i.e. ice inhibiting, sites on the molecules, while association of the non-ice-bonding sides of the molecule may orient too many molecules away from the ice face. Intentional steric hindrance and care in positioning polar groups can prevent unwanted self-association.

Naturally occurring molecules, such as simple sugars, polysaccharides and arabinoxylans that contain relatively large numbers of hydrophilic groups, have been found to produce weak thermal hysteresis. Some known AFGPs that act as natural IIDs consist of disaccharides linked to a polypeptide chain (often comprising several Ala-Ala-Thr repeats). In the same way, synthetic IIDs can be produced or synthesized that comprise, for example, saccharides or polysaccharides linked to a carbon polymer backbone, such as that found in polyvinyl alcohol (PVA). In this example, synthesis may be achieved by production of monomer units with saccharide side chains which are then polymerized, or by reaction of saccharide units with a preformed polymer backbone. Optimal distances between functional units can be achieved by controlling, in each monomer unit, the number of carbon atom units that possess condensation sites for the saccharide side chains. For example, C—C—OH, C—C—C—OH or C—C—C—C—OH repeats would space side chains by 1, 2 or 3 carbon atoms, respectively. Not all possible saccharide acceptor sites need be occupied to attain useful activity. Of course, this approach can use any substituents that possess requisite ice binding activity, not just saccharides. In fact, side groups, such as OH groups, may be left underivatized. For example, the polymers $$R(CHOH(CH_2)_3)_nR \qquad (1)$$

and $$OH(CH_2)_3CHOH(CH_2)_2CHOHCH_2OH \qquad (2)$$

where n is 2 to 3000, preferably, 2 to 500, and more preferably, 3 to 200, and R is any reasonable group such as an organic group such as an alkyl (e.g. $CH_3$) or hydroxyl group or a hydrogen atom, should be both easily synthesized and active. Designed structure (2) has been synthesized. Its predicted molecular mass was 179.1205, and its measured mass was 179.128; mass spectra confirmed that the synthesized molecule was made correctly.

Another molecular class useful for forming polymeric IIDs is the sulfhydryl (—SH) containing compounds. In this example, relatively low molecular weight monomers with ice-crystal lattice matching character are synthesized with one or more sulfhydryl groups at appropriate positions. Upon oxidation, the sulfhydryl groups react to form disulfide bridges that link the low molecular weight monomers to one another to produce higher molecular weight IIDS. The sulfhydryl groups on each monomer should be positioned to avoid steric hindrance that would prevent monomers from binding to the ice surface, following the polymerization reactions. Steric hindrance can be avoided, for example, by placing sulfhydryl groups above or parallel to the plane of the molecules, thereby allowing relevant hydrophilic groups on the IIDs to interact with the ice. The oxidation of two thiols (sulfhydryl containing compounds) to form such a disulfide bridge can be brought about by using mild oxidizing conditions, and in this way, the rate of polymerization and therefore the molecular weight distribution of the resulting IIDs can be controlled to some extent. Also, the ratio of mono- to poly-functional sulfhydryl compounds can be varied to produce different molecular weight IIDS, using the same monomer species.

The polymerization process that forms active polymeric IIDs from relatively inactive monomer units can also be completed at the site of use of the IIDS. This in situ polymerization allows the user to deliver relatively low molecular weight monomers into an area where IID activity is required, for example, by spraying from an aerosol can, before polymerization takes place. Several chemical methods can be used to achieve the in situ polymerization, depending on the nature of the monomer. Examples of these methods include free radical initiation, anionic and cationic polymerization, and catalysis. If the monomeric species contain reactive groups such as sulfhydryl groups, polymerization can be brought about by using mild oxidizing conditions such as those mentioned above, including, for example, exposure of monomers to atmospheric oxygen after spraying.

A modular polymer is described in the examples and shown in FIGS. 4 and 5A–5C.

c. Molecular shape. At least some natural AFPs are linear polymers, and at least one appears to lie on or in the crystal as a linear rod (Yang et al., *Nature*, 333:232–237, 1988; Chou, *J. Mol. Biol.*, 223:509–517, 1992.) Although a linear arrangement of ice-bonding groups is useful for avoiding nucleation, another useful pattern of arrangement of ice-bonding groups is a branched structure, because it permits intensive coverage of the ice crystal surface.

Figure 3:
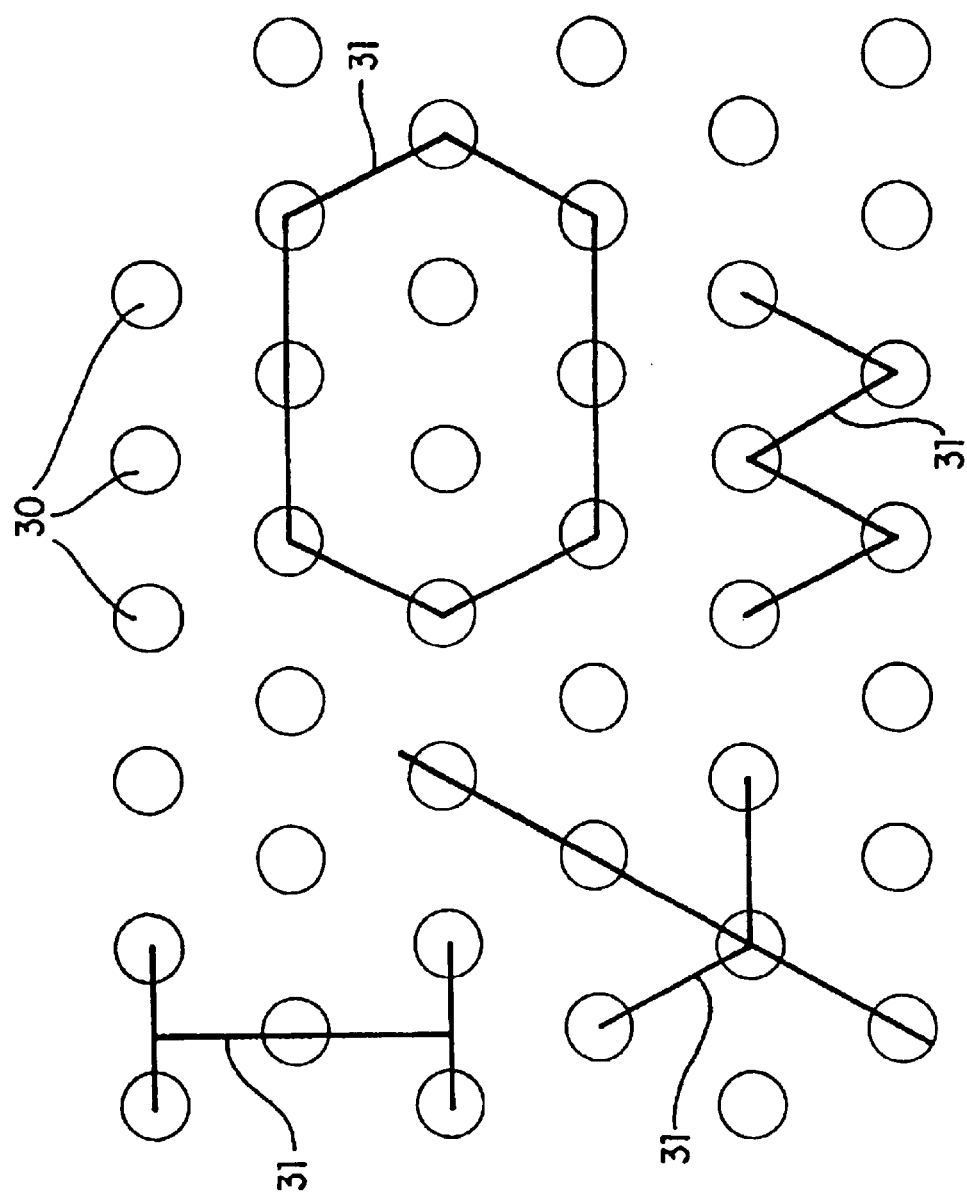
FIG. 3 schematically depicts various options or techniques for lattice matching using branched or ringed structures.

As shown in FIG. 3 (only upwardly-projecting ice vertices shown), structures 31 can bind the nearest available bonding sites, not just binding sites that happen to lie along a particular straight line. This can be achieved by using molecularly branched structures (such as rods with flexibly extending periodic "arms" such as "I" or "Y" or "X" shaped molecules), cyclic structures, "W"-shaped structures, or combinations and variations of these forms.

IIDs preferably include steric hindrance features ("bumps" or "standoffs") to avoid or limit self-association at the ice-bonding sides or the sides facing away from ice (the hydrophobic sides). Such features may include methyl groups, ethyl groups, crown ether protrusions, etc. Generally standoffs will be hydrophobic or weakly hydrophilic.

d. Amphiphilicity. Natural IIDs appear to act by placing ice bonding groups (e.g., polar or hydrophilic groups) on one side of the molecule and non-ice bonding groups (e.g., non-polar or hydrophobic groups) on the other, effectively attracting ice on one side and repelling water on the opposite side. This feature generally is preferred in synthetic IIDS, with the cautions indicated above about polar-polar or hydrophobic-hydrophobic interactions on the preferentially ice-binding and preferentially non-ice-binding faces of the IID, respectively.

e. Lattice matching. Lattice matching is fundamental to the binding of IIDs to ice. Lattice matching may involve direct hydrogen bonding to specific ice sites or bonding along electrical resultant vectors on the ice surface (Yang et al., *Nature*, 333:232–237, 1988). The structure of a normal ice lattice is known. Furthermore, this structure is essentially invariant with temperature, the 4.52 Å spacing decreasing by only 0.04 Å and the 7.36 Å spacing decreasing by only 0.05 Å as temperatures decrease from 0° C. to −196° C. Thus, to a first approximation, lattice matching provides clear design information that can be used to match repeat distances in ice to repeat distances in synthetic IIDs. Ice contains several additional lattice matching distances. These include distances of 16.7+0.5 Å for molecules aligning along the $01\bar{1}2$ axis and 6.3+0.4 Å for molecules aligning along the $20\bar{2}1$ ice plane. Bonding sites related by the longer distance form an essentially isosceles triangle of two approximately 16.7 Å sides separated by an approximately 48±2° angle. The approximately 6.3 Å bond length repeats in an essentially linearly disposed pattern.

Complexities are introduced by the mechanics of ice crystal growth in the presence and absence of IIDs. If a flat ice crystal face is presented, the exact positions of the oxygen and hydrogen atoms in that face are, to a first approximation, defined, and a match to these positions can be sought. In a growing crystal, however, newly-added water molecules will be found on the otherwise-flat primary crystal face, potentially interfering with IID adsorption for steric and geometric reasons. Addition of ice to the crystal face will create some disorganization of the crystal face that should be taken into account, and generally ice crystal faces are considered to be molecularly "rough". IIDs are preferably designed to accommodate this situation by "recognizing" steps or bumps on the ice faces and binding to the step or bump sites specifically, or by being step-shaped or concave themselves. The hydrogen bonding sites on step- or bump-recognizing IIDs will bind to ice molecules in two or more lamina of the ice crystal. A means of accomplishing these objectives is described below.

When IIDs 19 are present that induce the growth of spindle-shaped ice crystals 22 in the direction of the c axis 16 (FIG. 1B), one can remedy this "C growth" by adding an IID that binds to the basal plane 18 of ice (the face that faces along the c axis direction 16. In addition, the side of a spicule may not necessarily resemble well either the normal prism or basal plane structure and an IID designed to match this spicule surface may prevent or help to prevent this type of surface from forming. Therefore, an analysis of the structure of the spicule surface is also advantageous for designing IIDs lattice matching to this unusual surface.

f. Rigidity. Synthetic IIDs are preferably structurally rigid. This can be particularly important when fairly large (5 or 6 or more monomers) polymers are created, because free or limited rotation from monomer to monomer rapidly creates a proliferation of different conformational forms of the polymer, most of which will not bind properly to the ice surface. Rigidity allows the IIDs' structure to be well defined, which is both a design advantage and a physical functional advantage in performing lattice matching to a well-defined complementary surface, such as that of an ice crystal.

g. Orbital Steering. A particularly advantageous aspect of the process for defining IID structures is the concept of orbital steering. Orbital steering relates to designing bonds into the IID molecule so that lone pair electron orbitals or bonding hydrogen atoms are forced into or are allowed to occupy definite positions and orientations. The usual paradigm of matching oxygens or nitrogens in an AFP with oxygens in ice neglects the fact that a) it may be hydrogen in ice rather than oxygen that is actually being bound, and b) both hydrogen and lone pair electrons of oxygen in ice are located at a 104.50° angle with respect to each other.

Figure 6:
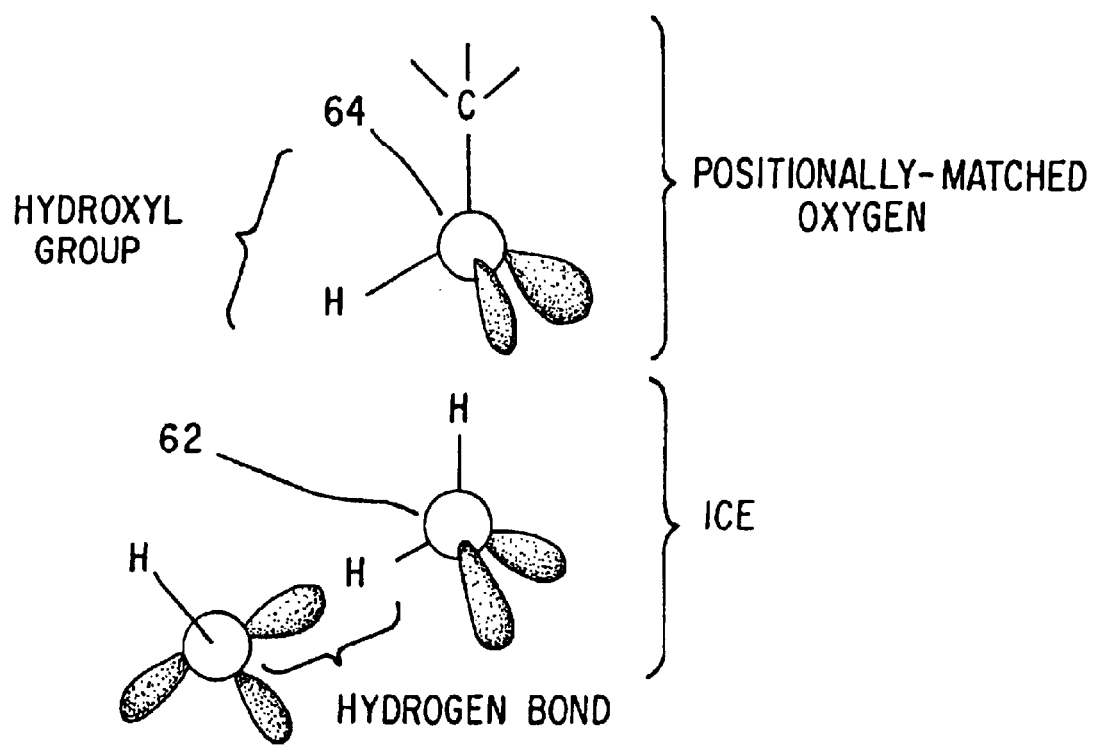
FIG. 6 shows a relationship between the lone pair electrons of a hydroxyl group and the bonding sites in ice that can exist when the oxygen of the hydroxyl group is merely positioned directly above an oxygen atom in ice.

FIG. 6 shows one possible effect of matching oxygen positions in a molecule with oxygens in ice lattice sites as has been commonly related in the literature to be an ideal strategy for ice bonding. The example shown uses the basal plane as the bonding surface for the IID. The oxygen positions are superimposable, but the bonding is weakened by failure of the orbitals in ice to align properly with the orbitals of the binding group to permit proper hydrogen bonding. "Orbital steering" provides an exact orbital orientation which should be more effective for binding to the ice lattice than just a local electron density increase designed into "non-orbitally steered" IID molecules.

Similar problems are found in natural AFPs. Orbitals are not aligned properly for proper hydrogen bonding. Despite this, natural AFPs are effective, but are not as effective as synthetic IIDs that can be designed to achieve precise orbital alignment.

One useful means to accomplish orbital steering is to incorporate the bonding atom into a ring structure analogous to the way in which oxygen is incorporated into the "backbone" ring structure of glucose in its closed form. The positioning of the bonding atom in the ring forces the lone pair electron orbitals of that atom to assume specific positions and these specific and predictable positions on different atoms can be arranged to be parallel to each other and spaced appropriately for bonding to appropriate atoms in ice.

In addition to oxygen, other elements, such as nitrogen, having lone pair electron orbitals can be used in much the same way as oxygen, albeit in slightly different architectures. For example, nitrogen can serve as a vertex between 3 carbon atoms.

Chirality of the bonds is important. If an alternate enantiomorph is used, the lone pair orbital electrons will not be optimally oriented.

Figure 1B:
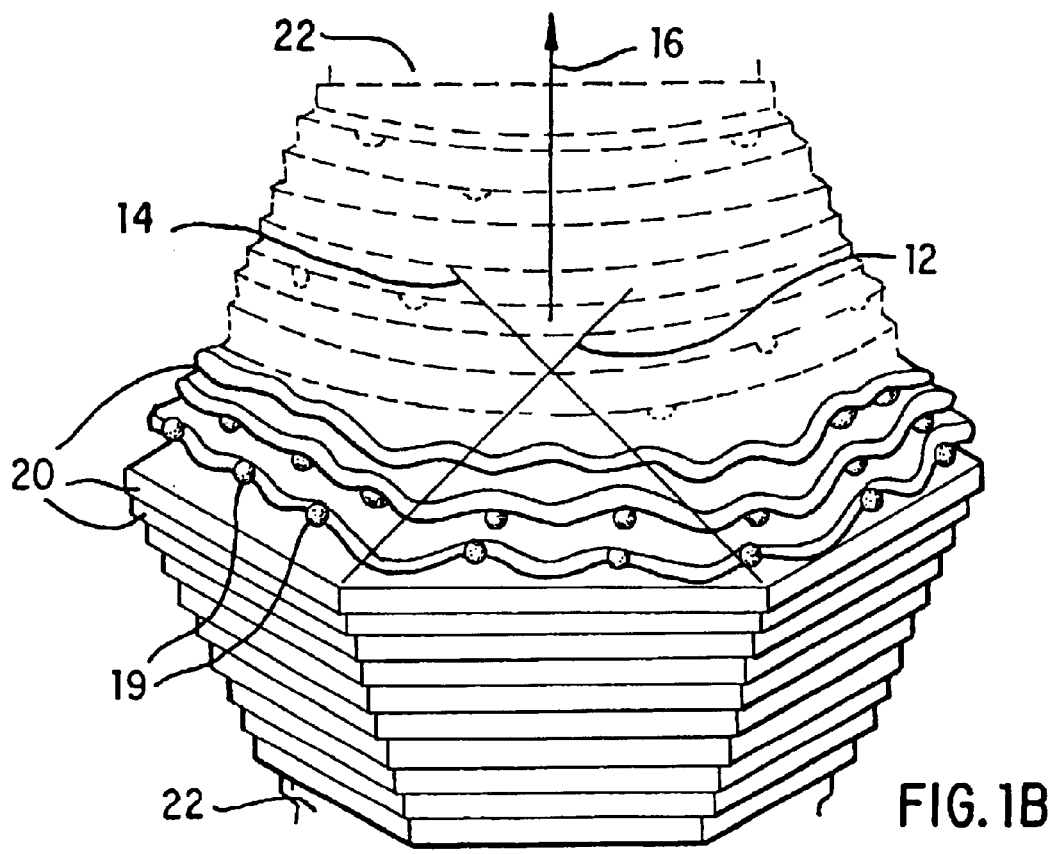
FIG. 1B shows an ice spicule formation in the presence of a and b axis inhibitors.
Figure 2A:
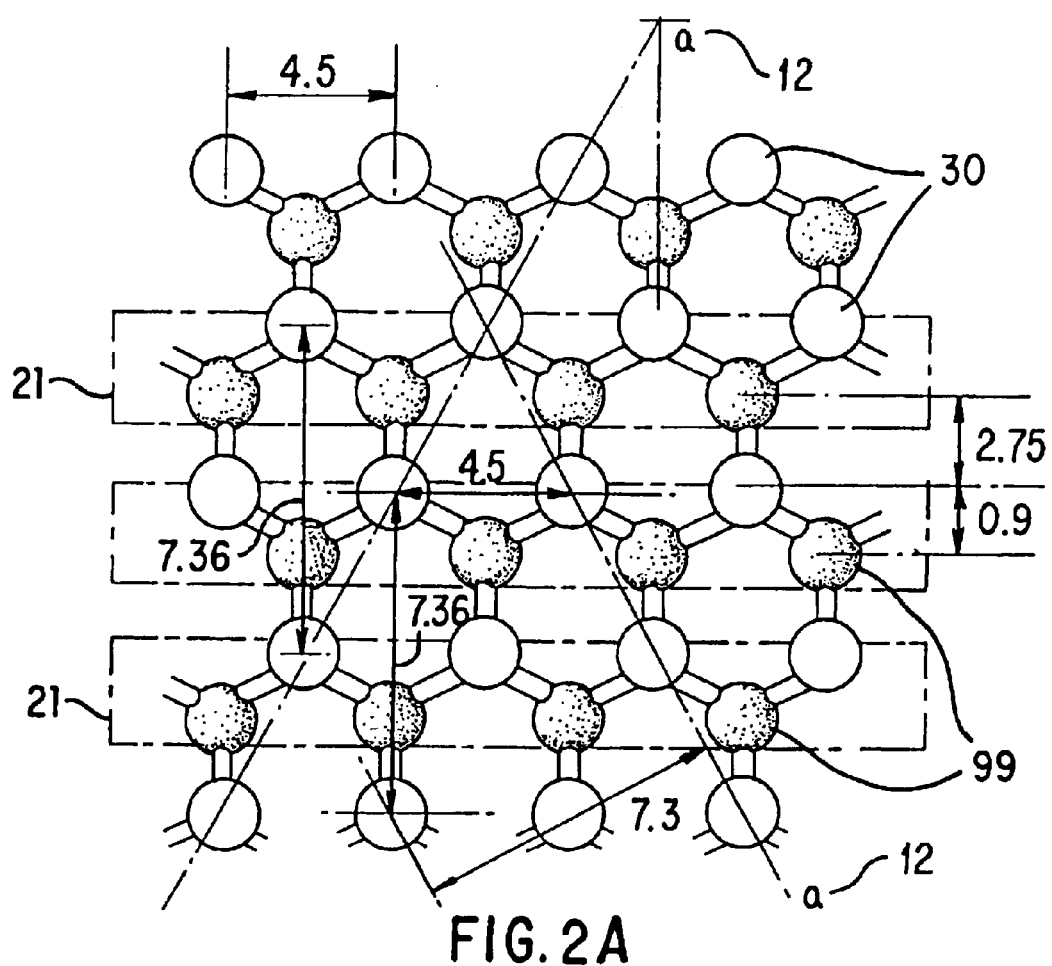
FIGS. 2A–2D show the lattice structure of the basal plane 0001 (FIG. 2A) and the prism faces (FIGS. 2B–2D) of an ice crystal.
Figure 2B:
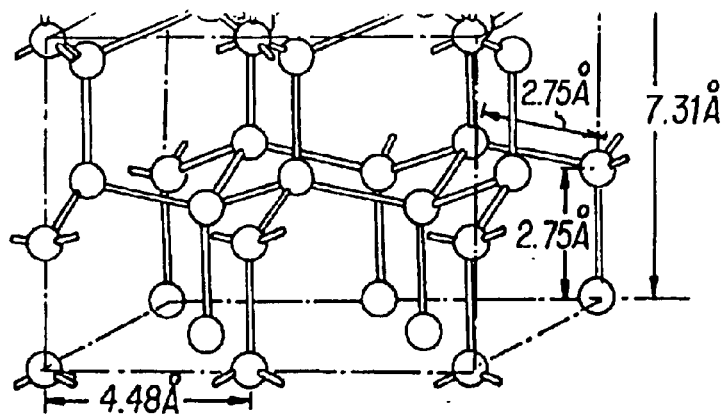
Figure 2C:
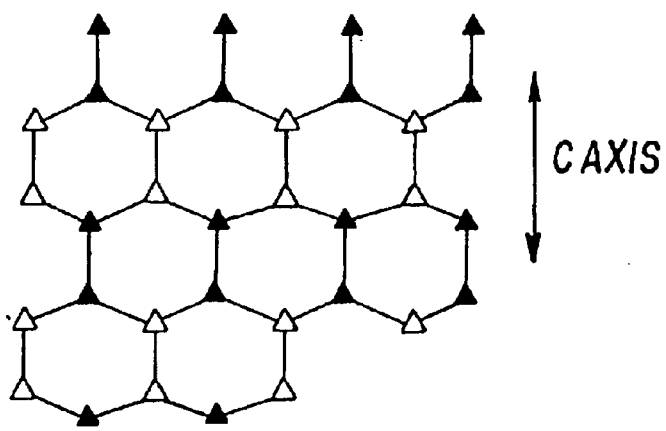
Figure 2D:
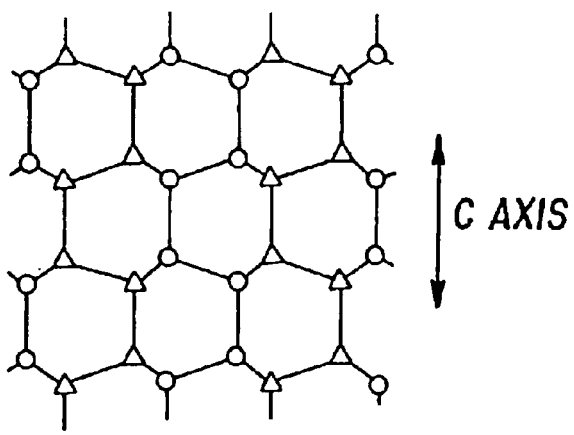

Surprisingly, particularly useful examples of orbital steering have been discovered that do not employ atoms incorporated into ring structures but that instead employ only freely rotatable ice-bonding groups. This novel form of orbital steering is treated below at length in section i.

h. Surface characteristics and acceptable void areas. As illustrated in FIG. 1B, natural IIDs 19 cover only a small fraction of the ice crystal surface, yet are effective. This is accomplished because growth inhibition is not purely a matter of steric interference with the approach of water molecules to and their adsorption on the ice surface. Rather, it is also a matter of the lack of lateral bonding sites for an adsorbed water molecule to provide stabilizing forces to prevent spontaneous loss of the adsorbed water molecule back into the surrounding solution, in other words, a matter of the surface energy of ice (the Kelvin effect; see Mazur, *Ann. N.Y. Acad. of Sci.*, 125:658–676, 1965). Adsorption of IIDs indirectly creates an increase in ice surface energy between IID adsorption sites, thus producing an ice-retarding effect that extends many molecular diameters over the ice surface beyond the IID adsorption site itself as indicated in FIG. 1B.

The value of this effect decreases as the extent of supercooling of the liquid medium increases and the driving force for crystallization thus increases to overcome the higher ice surface energy barrier to crystal growth. IIDs or IID elements therefore should be designed to be spaced appropriately for the extent of supercooling that is important for the particular application at hand. Thus, for example, appropriate void spaces within toroid-like IIDs for protecting orange groves may be larger than appropriate void spaces used for food freezing and the latter void spaces may exceed those that are appropriate for biological cryopreservation.

The Kelvin equation describes the freezing point depression caused by forcing ice to assume a highly curved (high energy) shape in order to propagate through an aperture. This equation is also applicable to the freezing point depression caused by restricting ice surface area between both natural AFPs/AFGPs (Wilson, *Cryo-Letters*, 14:31–36, 1993) and synthetic IID molecules. Thus, in designing a circular IID, for example, this relationship establishes the diameter of the IID loop that will protect against ice crystal growth through the loop at a given level of bulk solution supercooling. If extreme extents of supercooling are required (as in organ vitrification), complete inhibition of crystal growth may not be feasible without complete coating of ice nuclei, but complete inhibition may be unnecessary if crystal growth is sufficiently slow. In the latter consideration, the smaller the loop diameter the slower the crystal growth will be, until the diameter becomes small enough to possibly induce ice nucleation activity.

i. The CHD motif: facile and pivotal orbital steering and atom positioning. One particularly salient IID motif, which is advantageous in the design and synthesis of effective IIDs, is the 1,3-cyclohexanediol motif (hereinafter the CHD motif). The CHD motif may be considered to specifically include "crinkle complementarity" in combination with pivotal or rotational orbital steering and non-nucleating bonding group density.

Figure 11A:
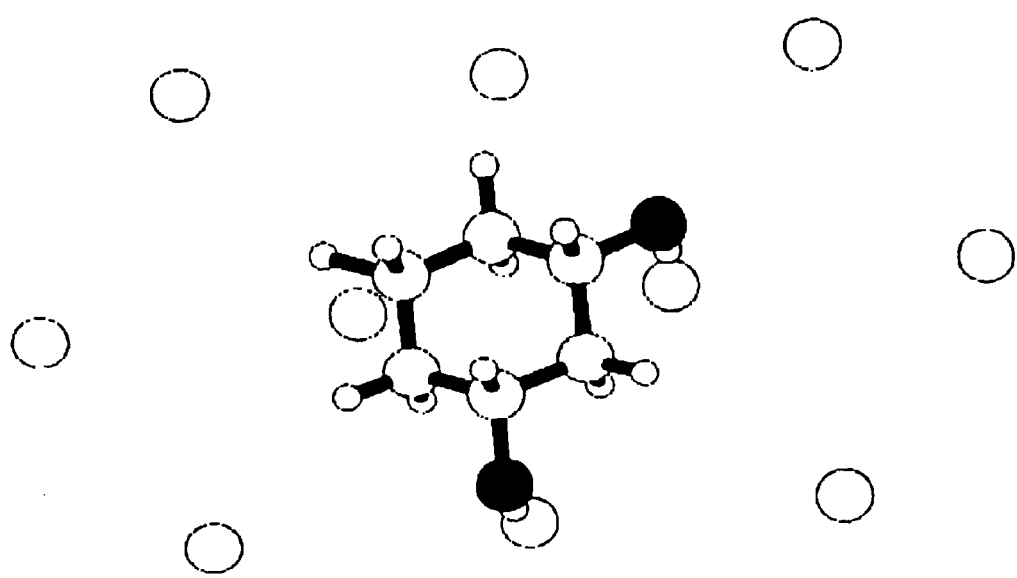
FIGS. 11A–11D show ideal prototypical ice bonding motifs, i.e., cis-1,3-cyclohexanediol (CHD) (FIG. 11A), the ability of trans-CHD to bond (FIG. 11B) to the prism face ridges of ice (FIG. 11C), and cis,cis-1,3,5-cyclohexanetriol (CHT) (FIG. 11D).

"Crinkle complementarity" is the positioning of ice bonding groups on a carbon backbone on consistently even or consistently odd carbons so as to match the up-down-up-down-up-down positioning of such carbon atoms in an aliphatic carbon chain to the up-down-up-down-up-down positioning of bondable vertices on the surface of the basal plane or other applicable site. It has been noticed for example that positioning OH groups on carbon atoms separated by a single carbon atom in 5 to 7-membered aliphatic carbon rings allows the OH groups to coincide with the upwardly-pointed vertices of ice which are the only vertices available for hydrogen bonding (FIG. 11A).

Taking the "crinkled" natures of carbon chains and of the basal plane into consideration allows not just superpositioning of hydrogen bonding groups over the bondable vertices of the basal plane, but also alignment between the bonding orbitals of the IID OH groups and bonding orbitals of the basal plane (orbital steering) (FIG. 11A, note hydrogens projecting directly downward from CHD toward the upwardly-pointing lone pair electrons on the bondable ice vertices illustrated), thus eliminating the problem illustrated in FIG. 6. By using free (rotatable) OH groups on the IID (rotational or pivotal orbital steering), it is possible for these OH groups to bond to underlying ice vertices regardless of whether the ice vertex presents a hydrogen atom or a lone pair electron cloud to the environment, because free rotation allows either the lone pair electron cloud of the IID oxygen or the hydrogen atom of the IID OH group, respectively, to bond to the ice vertex. This ability to match virtually any region of a target ice motif is a major advantage.

Figure 11B:
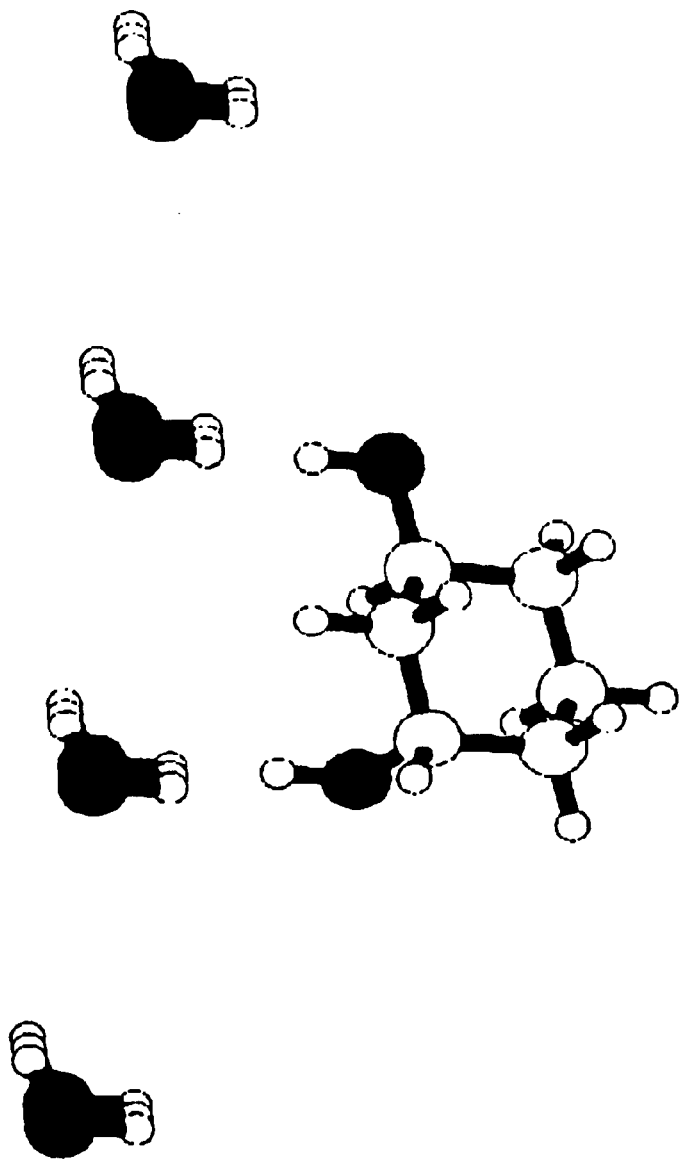
Figure 11C:
Figure 11C:
Figure 11C:
Figure 11C:
Figure 11C:
Figure 11C:
Figure 11C:
Figure 11C:
Figure 11C:
Figure 11C:
Figure 11C:
Figure 11C:

A racemic mixture of cis and trans-1,3-CHD is commercially available and has been tested for ice growth inhibiting activity, which had not been anticipated in the prior art. FIG. 11B shows that the trans isomer is capable of bonding to the bondable sites on the prism face of ice (FIG. 11C), which may explain why the racemic mixture is as effective as it is. (Note: FIG. 11B shows hydrogen atoms of the IID pointed at hydrogen atoms on the prism face only for ease of visualization of the loci of the IID's lone pair electrons when the OH groups rotate to present lone pair electrons toward the ice hydrogen shown.)

As illustrated in the examples below, the CHD motif is a non-nucleating motif that is biologically non-toxic and is commercially available as a starting material for synthesis of non-commercially available CHD polymers which are predictably of higher activity.

A related molecule, cis,cis-1,3,5-cyclohexanetriol (CHT) (FIG. 11D), which was found to have thermal hysteresis activity (see example below), is also available to use as a starting material for synthesis of CHD polymers, one OH of the cyclohexanetriol being used as a site of cross-linking to other cyclohexanetriol monomers to form the polymer. Neither CHD nor CHT have been suspected to have ice growth inhibiting properties in the prior art.

Figure 12:
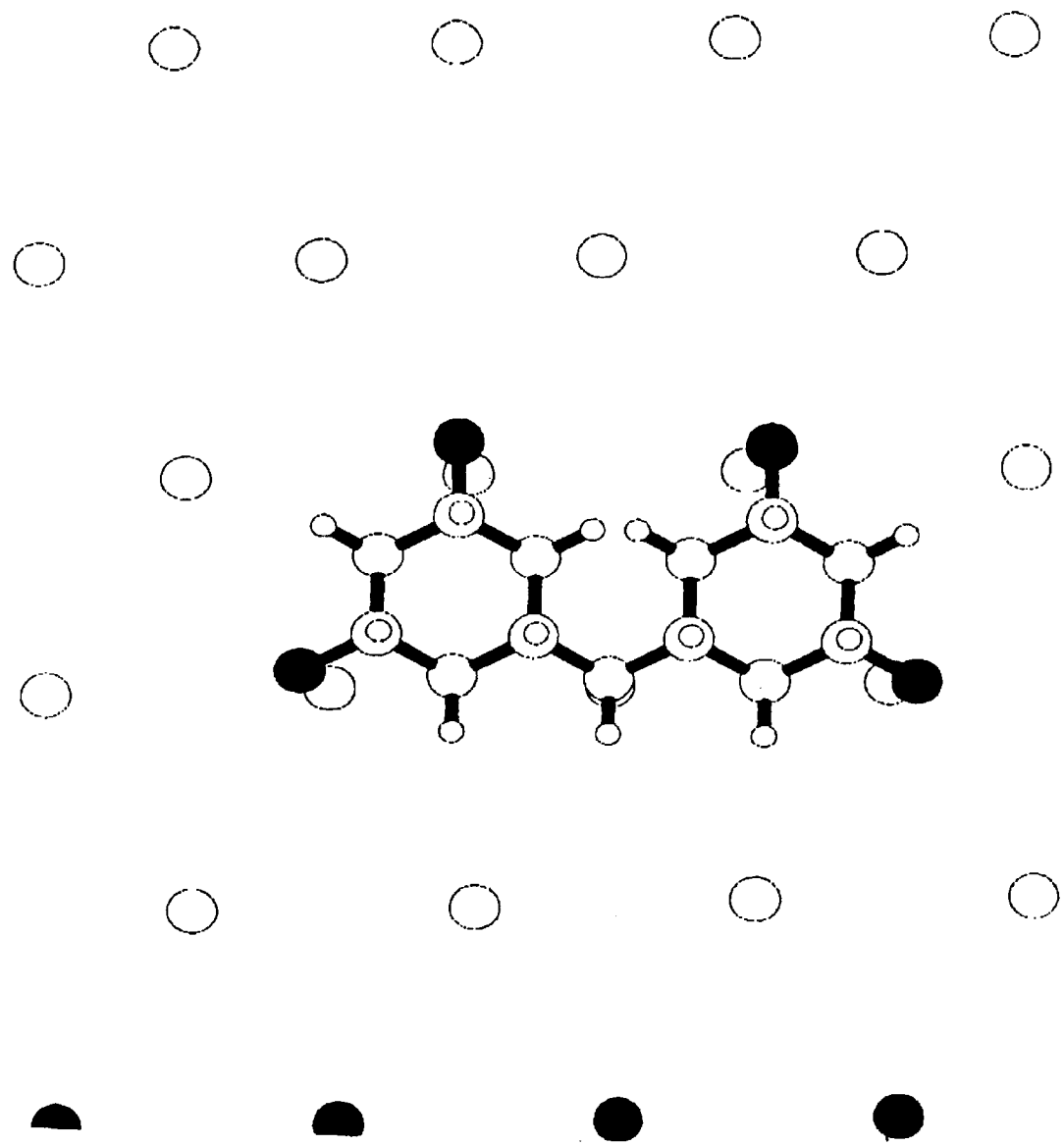
FIG. 12 shows one mode of polymerization of CHT or CHD.
Figure 13:
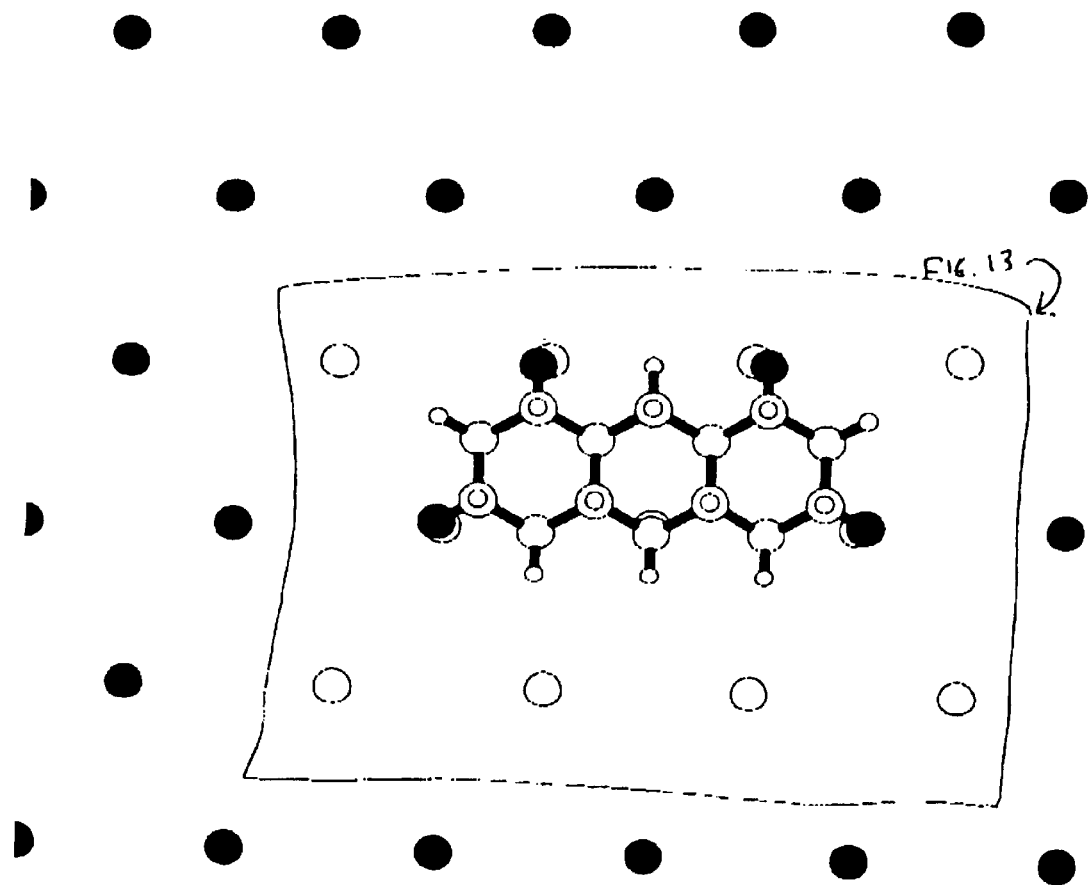
FIG. 13 shows a second mode of polymerization of CHT or CHD.
Figure 14:
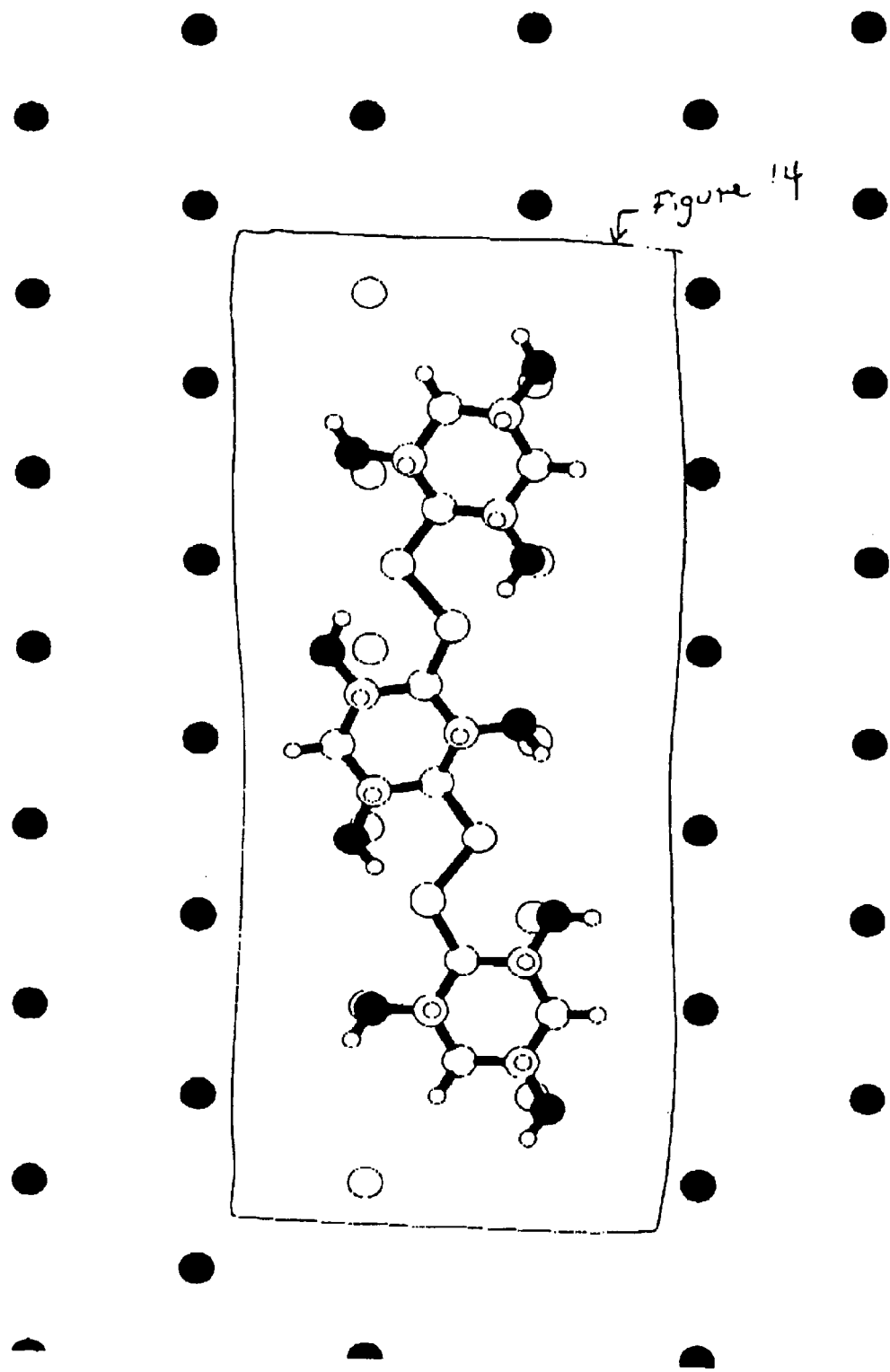
FIG. 14 shows a further mode of polymerization of CHD or CHT.

Although, as illustrated below, CHD is extremely effective at inhibiting ice crystal growth, it forms only two bonds per molecule. A recent study on the binding of a recombinant globular eel pout AFP type III protein to ice concluded that formation of about 4–5 bonds to ice (about 1 bond per 1,300 daltons) was needed to form an essentially irreversible association between the protein and ice ("Structural basis for the binding of a globular antifreeze protein to ice", *Nature* 384: 285–288, 1996; Z. Jia, C. I. DeLuca, H. Chao, and P. L. Davies). A similar absolute number of bonds can be formed per CHD-type IID using a CHD motif dimer (FIGS. 12 and 13) or trimer (FIG. 14), all of which retain ice bonding geometry and ice complementarity. FIG. 14 illustrates the linking of CHD monomers using disulfide bridges (cross-hatched atoms). Alternatives to disulfide bridges include the ring structures, single carbon, and double bonded carbons.

Figure 15:
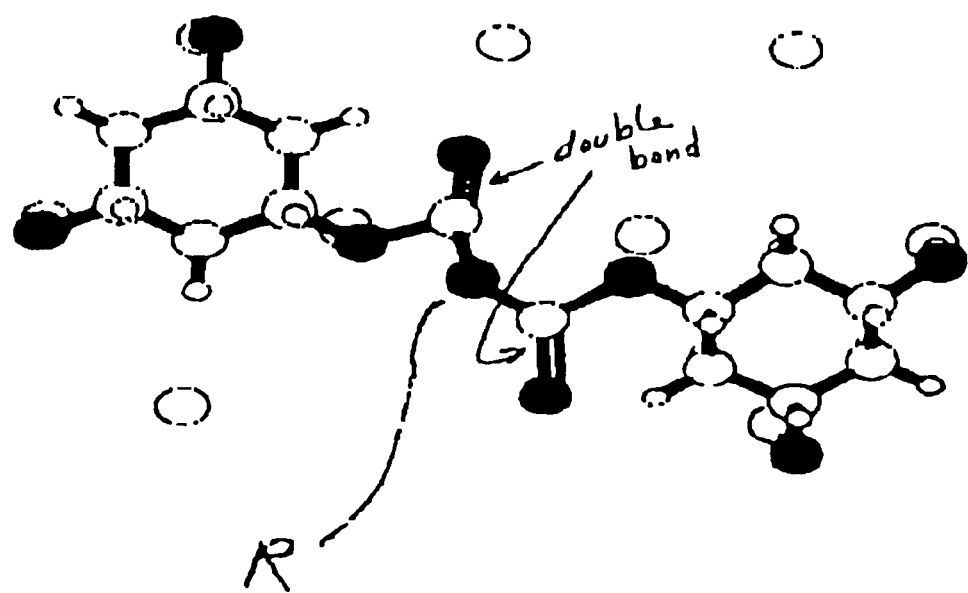
FIG. 15 shows a loose mode of polymerization of CHD.

FIG. 15 illustrates linking of CHD monomers using hydrophillic chains such as succinate, 4'-phosphopantetheine, RNA, etc. Such bridges will sterically interfere with ice growth between CHD moieties while allowing the CHD moieties to bond individually to the ice lattice.

j. IIDs that nucleate ic: the CHT motif. While the application of IIDs emphasized herein is to inhibit ice crystallization, another variant on IIDs is IIDs that create the ice interface that they dope, i.e., IIDs that are effective nucleators. There is a vast commercial potential for nucleators in cloud seeding, snow making, use as molecular tags (i.e., using the nucleator as a "reporter" of the presence of the linked molecule of interest, rather than using fluorescent tags, for example, since in principle a single molecule might be detected by the ability of its tag to nucleate a volume of water), and other areas. It has been observed that cis,cis-1,3,5-cyclohexanetriol (CHT), which is identical to CHD but with the inclusion of one extra ice bonding group per cyclohexane moiety, is a good nucleator of both dilute and concentrated solutions. Specifically, CHT was found to nucleate water and concentrated solutions of cryoprotective agents (containing dimethyl sulfoxide, formamide, and 1,2-propanediol). The CHT motif, and particularly CHT polymers, thus provide a valuable ice nucleating molecular family.

Figure 11D:
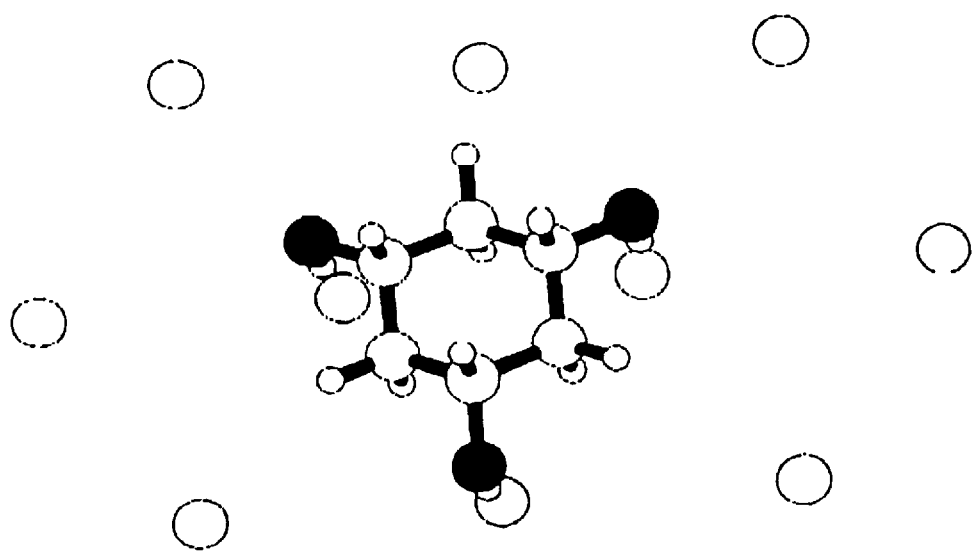

The number of bonding sites in CHT is equivalent to one bonding site per 45 daltons of IID, with the bonding sites arranged in the highest density per unit area that is physically possible (FIG. 11D). The number of bonding sites in CHD is equivalent to about one bonding site per 58 daltons, arranged in a linear rather than in a maximally tight two-dimensional (triangular) pattern. These distinctions appear to define one boundary between IIDs that nucleate and IIDs that simply inhibit crystal growth. 6 w/v CHD did not nucleate VS4 solutions (containing a total of 34% w/v "DF" (DMSO and formamide in a 1:1 mole ratio and 15% w/v 1,2-propanediol, in a Euro-Collins vehicle solution) at temperatures between −70 and −45° C. (see examples below).

k. Template-mediated synthesis of IIDs. Ice nucleating agents (INAs) are the functional opposites of THPs. They induce ice crystal nucleation rather than ice growth inhibition. Both THPs and INAs clearly must have a structural relationship to ice. Whereas THPs bind to ice, they do not resemble ice. INAs, because they create ice, are considered to more closely "resemble" ice, either structurally (as in AgI, mica or cholesterol crystals) or in terms of having a surface energy that is similar to that of ice, as might be the case for *Pseudomonas syringae* nucleating sites. Parody-Morreale et al. (*Nature*, 333:782–783, 1988) showed that fish antifreeze glycoproteins inhibited nucleation by bacterial ice nucleators, suggesting that the antifreeze molecules bind to the nucleators due to the ice-like structure of the nucleators.

Routine assays for the inhibition of ice crystal growth are known (for example, see Knight, DeVries, and Oolman, *Nature*, 308:295–296, 1984). Another assay for binding activity is the ice crystal growth habit assay (Knight et al., *Nature*, 308:295–296, 1984). This assay is frequently performed using a microscope in conjunction with the Clifton Technical Physics (Hartford, N.Y.) Nanoliter Osmometer to observe ice crystal growth and melting (see, for example, Chakrabartty, Yang and Hew, *J. Biol. Chem.*, 264(19); 11313–11316, 1989). This assay technique can be used in an identical way to determine the activity of synthetic or isolated IIDs. The nanoliter osmometer can be used to investigate the effect of the IID on the growth of the ice crystal in each of the component crystallographic directions (i.e., on the crystal habit) (see, for example, Chakrabartty and Hew, *J. Biochem.*, 202;1057–1063, 1919). Assays performed with the nanoliter osmometer involve observing an ice crystal in a solution of the IID near the melting temperature. The difference between the temperature at which the crystal starts to melt, and the temperature at which the crystal begins to grow is a characteristic of an IID, termed thermal hysteresis, that is used to demonstrate ice bonding and growth-retarding activity.

EXAMPLES

Figure 4:
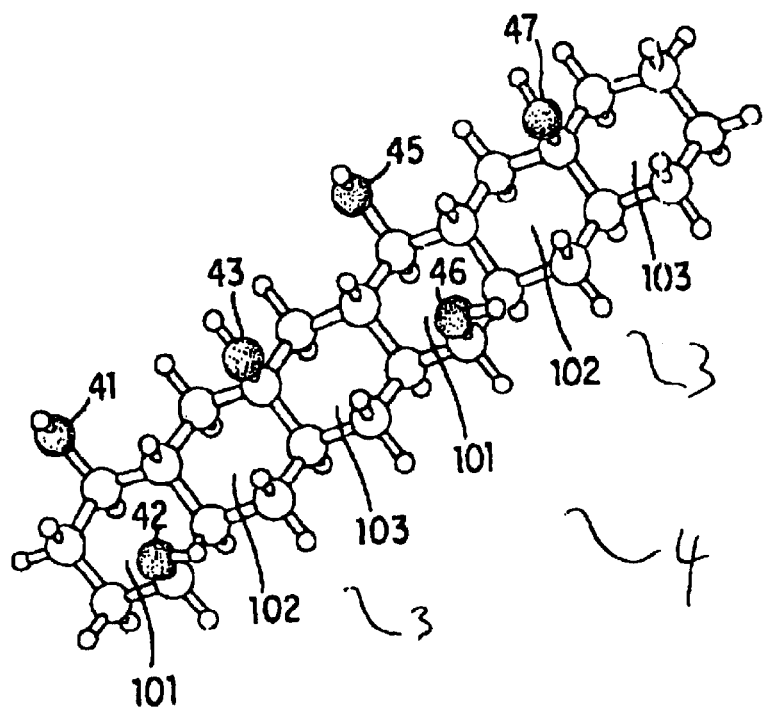
FIG. 4 shows an adaptable prototypical dopant molecule (IB1) with hydrogen bonding sites for bonding to an ice nucleating body.

A Generic IID. As noted above, the 37-amino acid flounder antifreeze protein forms as few as one hydrogen bond per eleven amino acid residues, or a ratio of one bond per 819 daltons or so of AFP. FIG. 4 shows a synthetic IID (IB1) (Structure 4) designed to have one bond per 75 daltons of IID. This IID was constructed and dimensions were determined using HyperChem, a computational chemistry software package that typifies software available to facilitate the preparation of novel IIDs given the principles described here. In this structure, the large open circles represent carbon atoms, densely stippled circles represent oxygen atoms that bond to ice, and small open circles represent hydrogen atoms.

Bonding sites are represented by the oxygen atoms 41–43 and 45–47. Structure 3 consists of three monomer rings 101, 102 and 103 that act as a supermodule that is repeated once. The spacing of oxygens across the width of the strip is precisely 4.50 Å (oxygens 41 to 42 and 45 to 46), and the nearest oxygen spacing along one edge of the strip is 4.55 Å, a negligible difference from the 4.52 Å spacing of ice oxygens. Furthermore, the spacing between oxygens 41 and 45, and between oxygens 42 and 46, is 7.54 Å, a close match to the 7.36 Å spacing of ice oxygens. The spacings across the strip (41 to 42 and 45 to 46) do not resemble the spacings in sugar molecules observed by DeVries, and the spacings along the strip edges also resemble no structure ever before contemplated. The combination of the axial spacings, e.g., oxygen 41 to 43 and 41 to 45, with the lateral spacings, e.g., oxygens 41 to 42, so as to match the triangular distribution pattern of bondable ice vertices on the basal plane, similarly represents a previously-unknown structure and motif.

This design illustrates the internal modularity of the IID (rings 101–103), the planar (and by implication the potentially ring-shaped nature) of the IID, the positioning of polar groups exclusively on one side of the amphophilic molecule, the use of at least moderate structural rigidity to ensure faithful positioning of bonding sites, the minimization of IID mass and local area, and the attainment of considerably more ice bonding per unit mass than is achieved by natural IIDS. The potential for inserting lateral polar groups for side-to-side hydrogen bonding into cooperative arrays is also evident.

Figure 5C:
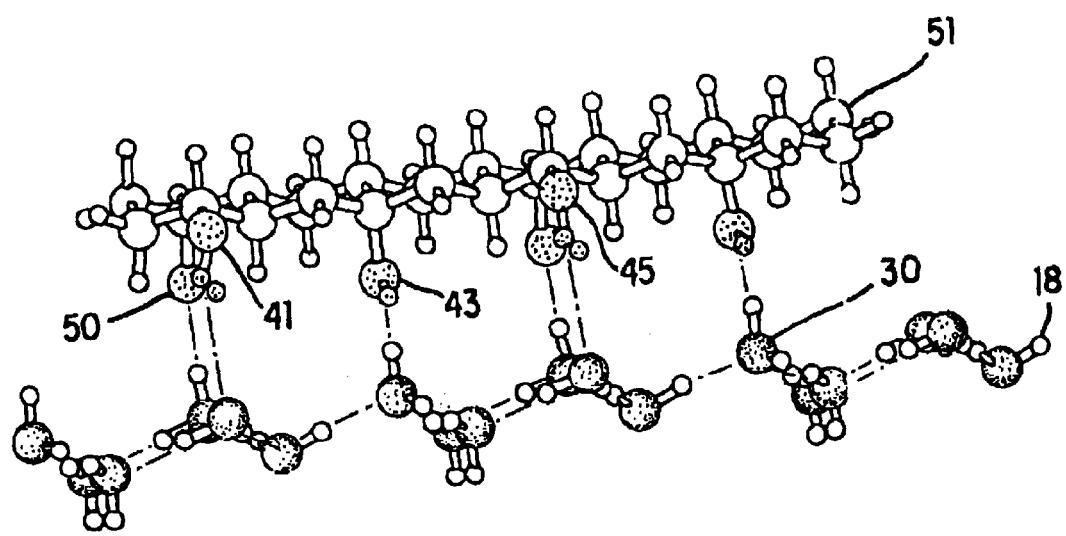
FIGS. 5A–5C show three views of an ice lattice structure with the dopant molecule of FIG. 4 attached.
Figure 5A:
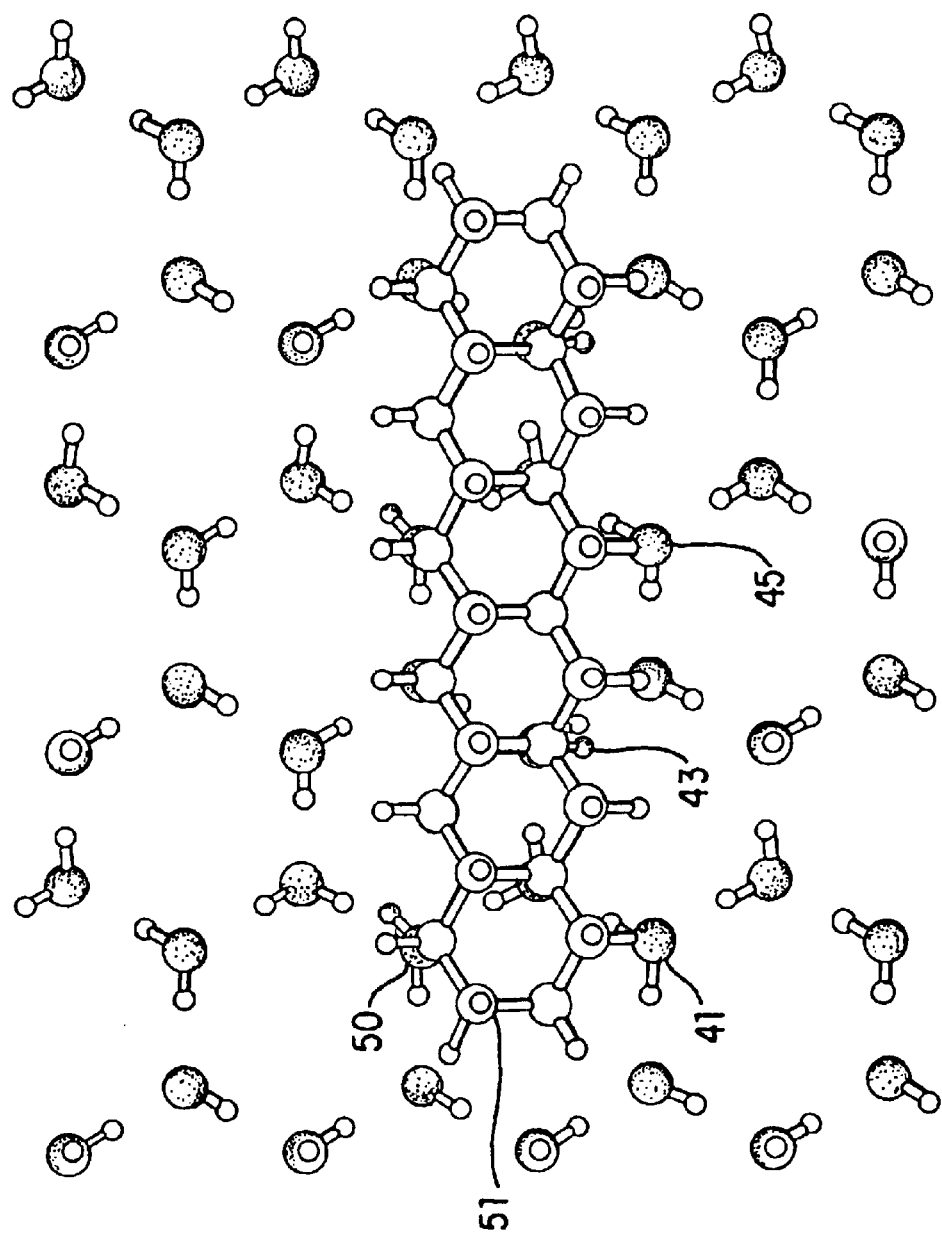
Figure 5B:
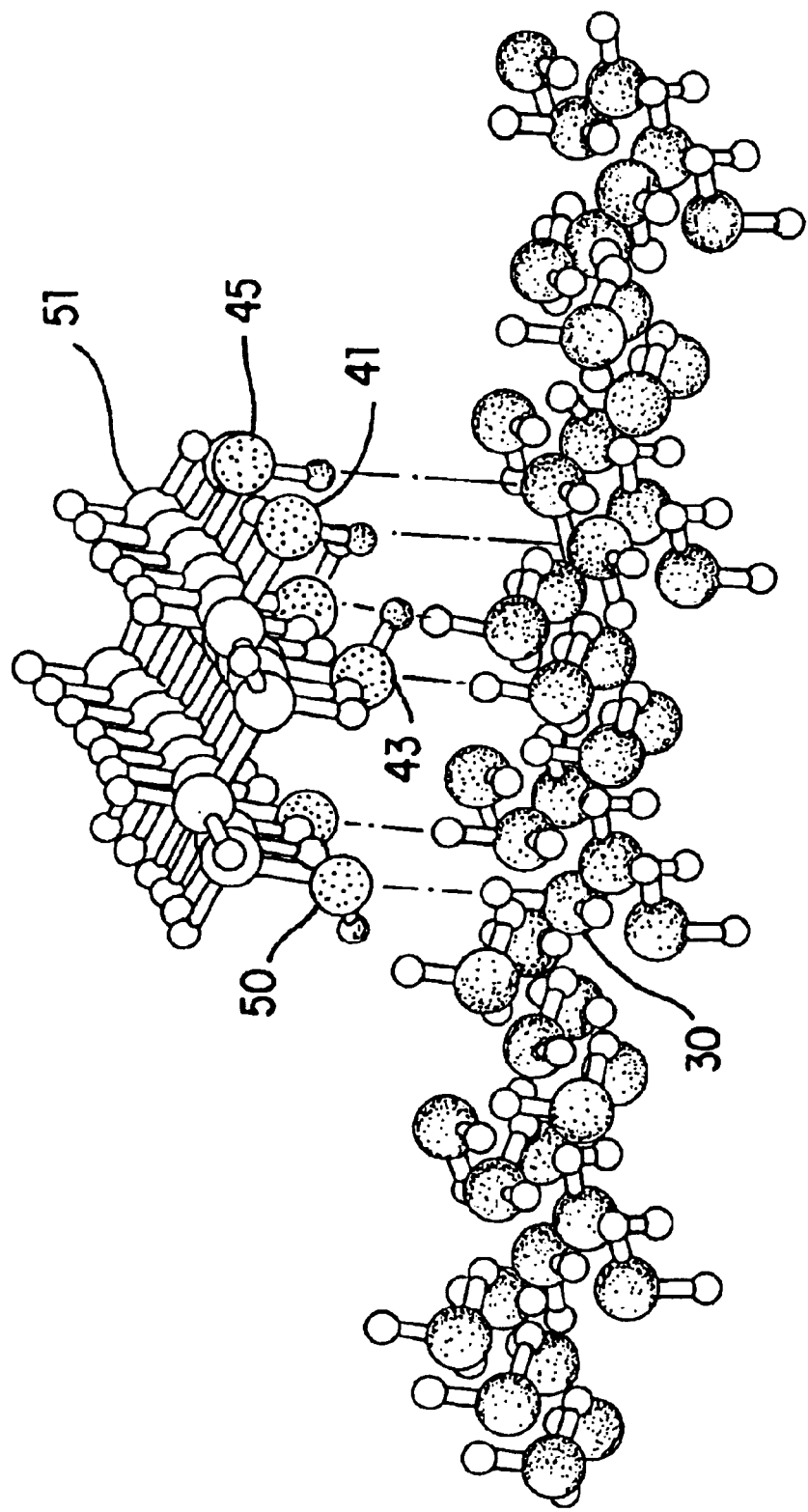

In FIGS. 5A–5C, oxygen atoms in the uppermost layer of the ice crystal 0001 basal plane surface 18, are shown as stippled circles. This ice crystal lattice was created using the computational chemistry package, HyperChem, and all inter-atomic distances and angles represent, as closely as possible, the published experimental values. The hydroxyl groups of IB1 are sparsely stippled to differentiate them from the oxygens and hydrogens of the ice lattice.

In FIGS. 5A–5C, 51 represents IB1 that has been rotated so as to face the basal plane surface to permit hydrogen bonding. For orientation some oxygen atoms of the IID (41, 43, 45) have been identified using the same numbering shown in FIG. 4. The diagram discloses that all available sites 30 are in fact bonded by the IID.

FIG. 5A presents a view looking down the c axis of an ice crystal, and FIG. 5B shows a perspective view of the same ice-IID complex clearly show the hydrogen bonding between the ice and the IID (the hydrogen bonds are shown as dashed lines and were predicted by HyperChem). FIG. 5C shows IB1 and only the water molecules of the ice lattice that lie directly below it, viewed from the side. This figure again shows that all available sites 30 are in fact bonded by the IID.

FIGS. 5A–5C emphasize the remarkable coincidence between the spacing of strategically-located hydroxyls on a graphitic "molecular pegboard" backbone and the 4.5 Å and 7.4 Å spacing of forward-projecting oxygen atoms of ice. Of the six oxygen atoms 41–43 and 45–47 (shown as the large sparsely stippled circles 50), all six are directly positioned over forward oxygen atoms in the ice lattice (shown as densely stippled circles), and the number of bonds/dalton for IB1 is over ten times the number identified for one antifreeze protein by Chou.

Of course, it should be understood that structures such as IB1 and other examples presented herein can be modified in any way that does not change the positioning of its ice bonding groups. For example, non-bonding hydrogens can be replaced by fluorines, chlorines, hydroxyls, etc., and carbon atoms can be replaced, where feasible, by oxygen atoms, so long as the basic structural shape of the IID and its basic "sidedness" (one side for preferentially bonding ice, one side for preferentially not bonding ice) are preserved. In addition, not every single ice bonding group of IB1, for example, need be present for it to remain an effective IID.

IB1 exemplifies one preferred class of dopant of the present invention that prevents ice crystal growth specifically in the direction of the c axis 16. When used in combination with an agent acting to block growth in the direction of the basal plane 18, such that all growth planes would be inhibited rather than only one, such an agent should avoid the lethal drawbacks of freezing cells that attend using only basal plane growth inhibitors. Furthermore, since growth in the direction of the c axis 16 ("C growth") is the limiting factor for supercooling in the presence of agents that adsorb to the prism face 20 (agents that block growth in the a axis direction, or "A growth"), C growth inhibitors used in combination with A growth inhibitors should enhance supercooling considerably over the supercooling achievable with A growth inhibitors alone and should also reduce freezing injury by preventing ice crystals from growing to large sizes during cooling as well as by preventing ice crystals from coalescing during warming, a process variously referred to as grain growth, recrystallization, or Ostwald ripening. Excessive growth of ice crystals is thought to be the primary means by which freezing damages the delicate extracellular structures present in organized tissues and organs and leads to the failure of these tissues and organs after thawing. Thus, the invention provides superlative control of ice crystal size and stability during cooling and warming, and provides an alternative approach to vitrification for the cryopreservation of complex systems, achievable with dramatically less technical complexity.

The structure 3 has the further advantage of being finely adjustable to any desired ice crystal morphology by virtue of the fact that the graphitic backbone's tetrahedral arrangement is clearly capable of following the ice lattice's tetrahedral arrangement. Carbon hexagons can be built out from the "strip-like" structure 3 shown into the surrounding plane in any manner desired, similar to patterns shown in FIG. 3. (FIG. 5A reveals that the geometry of IB1 is such that it effectively possesses branching character: if OHs 43 and 47 were omitted, IB1 would become one example of the "I" shape motif of FIG. 3.) Furthermore, carbon hexagons can be built upwards or downwards from the parent plane as well using a similar geometrical construction perpendicular to the plane depicted.

Evidently, the ability to create an extended matching pattern between structures like structural motif 3 and ice has not heretofore been recognized. DeVries noted one sugar OH—OH spacing of 4.5 Å in isolation in antifreeze glycoproteins containing the N-acetylgalactosamine residue on a repeating Ala-Ala-Thr structure (DeVries, Comp. Biochem., 73A:627–640, 1982), but this sugar spacing resulted from a different, more limited geometry not suggestive of artificial IID motifs as presented here.

Figure 7:
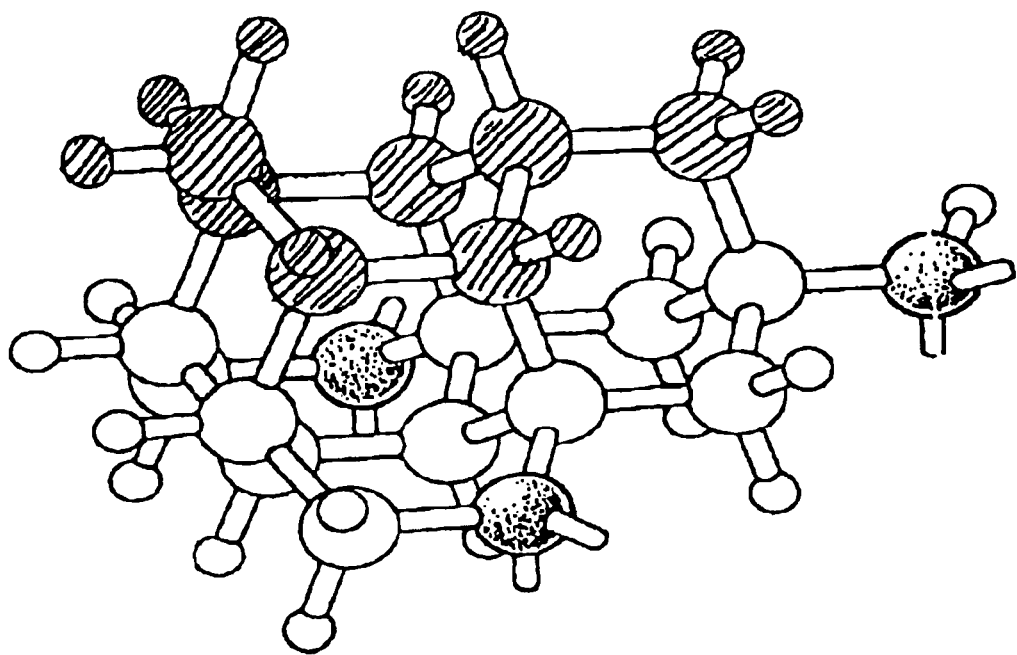
FIG. 7 shows the steered orbitals (two in rings, one freely rotatable) of an example artificial IID (IB2) arranged in such a way that they form an almost perfect match to the hydrogens of the basal plane of ice.
Figure 8:
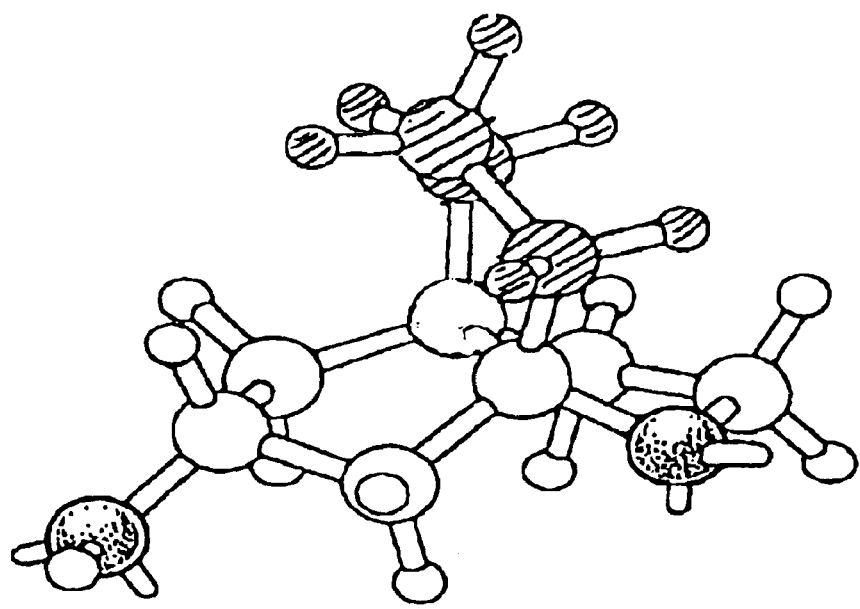
FIG. 8 shows a second example of an orbitally steered artificial IID (IB3) in which one oxygen is steered by being locked within a ring structure and the other is located in a permissive position for rotation into the correct orientation.
Figure 9:
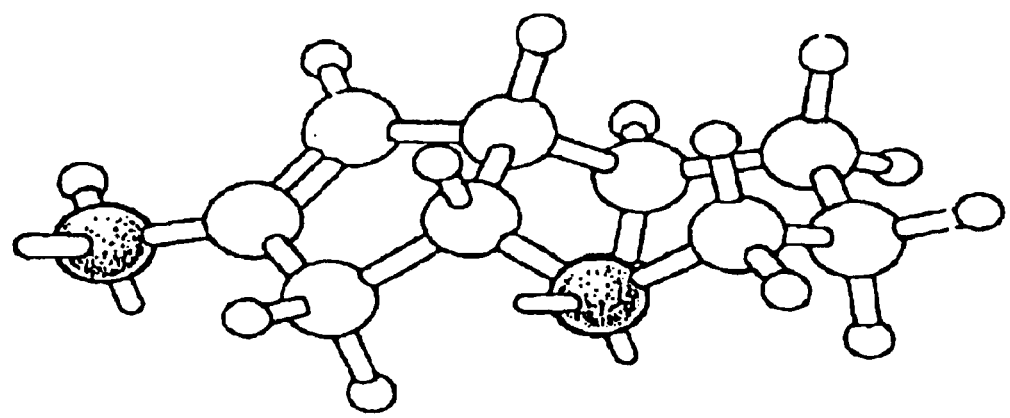
FIG. 9 shows a third example of a mixed ring-steered and rotationally-steered IID employing the same principle as that employed in IB3 but using a different physical embodiment.

Orbitally steered IIDs. FIGS. 7–9 show molecules with oxygen atoms bound in such a way as to orient the lone pair electrons from each oxygen atom into definite ice-bondable positions relative to those of the other oxygen atoms.

In FIG. 7, 2 oxygens are "locked" into a ring and one oxygen is allowed to freely rotate. In FIGS. 8 and 9, one oxygen is "locked" and one freely rotates, being positioned to allow its orbitals or bound hydrogens to rotate into an alignment parallel to that of the locked oxygen atom's bonding orbital(s).

In other words, this approach combines such "locked" atoms with atoms that are free to rotate about a single bond but whose rotating orbitals are capable of assuming positions that are approximately parallel to and spaced appropriately from fixedly "steered" orbitals so as to allow bonding to atoms in ice.

FIG. 7 represents a prototype orbitally-steered IID that achieves the goal of bonding all three vertices of an ice oxygen hexagon when all such vertices terminate in a hydrogen atom. The lone pair electrons of the stippled oxygens project directly downward from the IID and align with great fidelity with the ice hydrogen atoms, to form three strong hydrogen bonds. The positions of two of these orbitals are not freely movable and are therefore correctly aligned for ice bonding at all times. This arrangement is referred to as locked "orbital steering" or more simply as fixed "steering" in this application. The third oxygen, while free to rotate, is constrained to a position that allows its orbitals to align with the fixedly "steered" orbitals of the locked oxygens during rotation. This feature steers the bonding orbitals when they rotate to the proper degree and is therefore considered to be a form of weaker orbital steering referred to herein as "pivotal orbital steering" or "rotational orbital steering" or the like. This molecule attains a bonding density of approximately 1 bond per 95 daltons, a ratio that compares favorably with the 1 bond per roughly 422 daltons representing the optimum bonding density reported by Sicheri and Yang (see above). The spacing of the locked oxygens is 4.87 angstroms and the spacing between each locked oxygen and the rotationally free oxygen is 4.58 angstroms.

This particular prototype is chosen for this example also to illustrate the principle of building IIDs that have great structural rigidity to prevent the molecule from flexing and thereby changing the orientation of its ice bonding groups from bonding orientations to non-bonding orientations, as may happen in a simple hexagon, for example when it converts from the "chair" form to the "boat" form or vice versa. The degree of structural control built into the molecule shown in FIG. 7 (IB2) is greater than will often be desirable for easy synthesis, but vividly illustrates the principle of structural control. Compromises between rigidity and function can be made depending upon the requirements of the IID and the costs and practicality of synthesis. IB2 would, for example, normally be prepared with the optional (cross-hatched) atoms omitted.

FIG. 8 illustrates a considerably simpler molecule (IB3) that combines less elaborate structural control of one locked oxygen with rotationally permitted alignment on the part of a second oxygen. The structure, consisting of three 5-membered rings sharing a common pair of bridge carbons, could optionally be simplified by deleting the atoms (shown with cross-hatching) that form the third, oxygen-free ring which helps to establish the chirality of IB3. As shown, the bonding density is one bond per 84 daltons, and with the three carbon deletion would be one bond per 63 daltons. The oxygen-oxygen separation distance is 4.55 angstroms. In addition, molecules of IB3 can be tethered or rigidly linked together at proper spacings and angles so as to summate bonds over several IB3 monomers for greater overall bonding stability, as further discussed below for the CHD motif and the CHT motif.

FIG. 9 represents a second embodiment of the concepts illustrated in FIG. 8 (IB4). Again, a fixedly steered orbital can align with a rotationally steered orbital to produce a very local lattice match. The stippled oxygens are separated by 4.41 angstroms. The bonding density is about one bond per 77 daltons. IB4 monomers can be linked as needed to summate bonds over several monomers as for IB3. Note inclusion of one double bond in the 5-membered ring of IB4.

Figure 10:
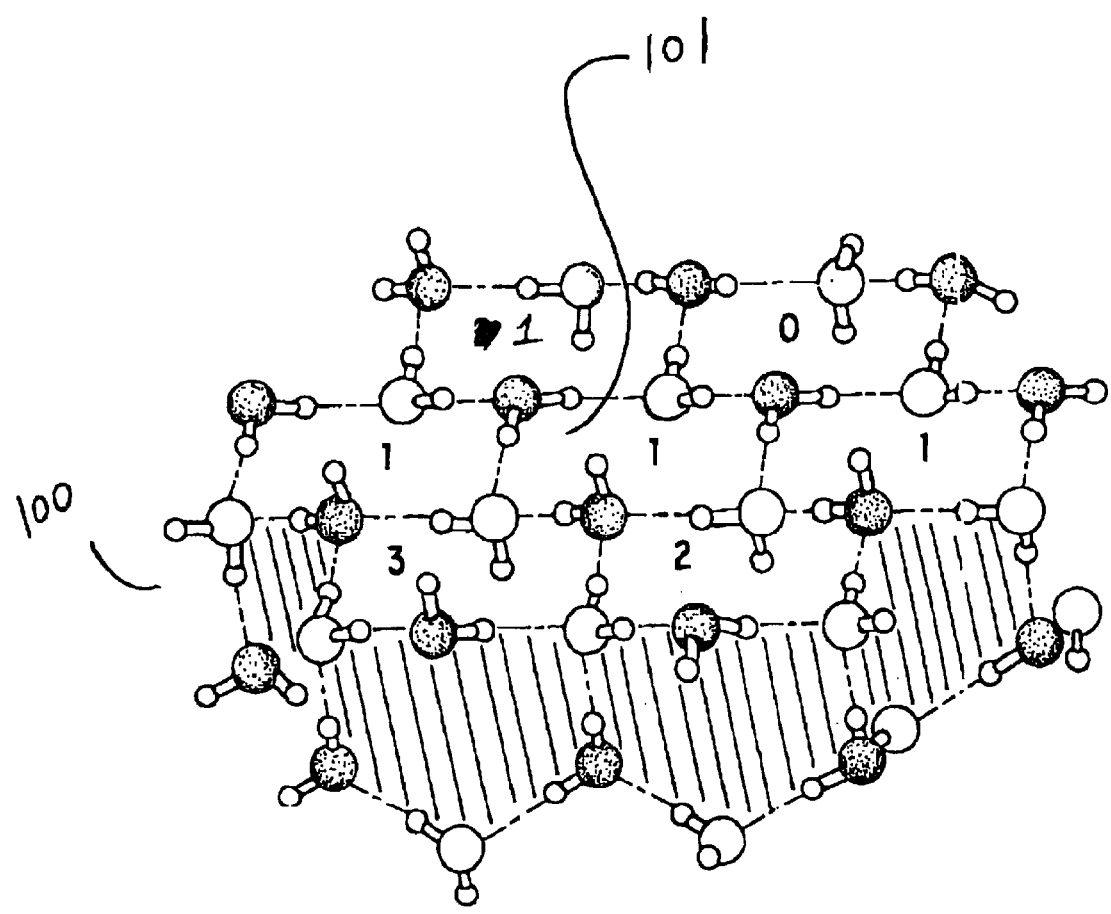
FIG. 10 shows the surface, in atomic detail, of the smallest ice crystal that resembles the macroscopically visible plate-like, hexagonal ice crystal shape, and shows the randomness of the upwardly-projecting vertex bonding features (hydrogens or lone pair electrons) of the surface hexagons.

FIG. 10 represents the simplest aggregation of water molecules 100 that retains the familiar hexagonal plate structure of macroscopically visible ice growing in solution. Water molecules fit into the lattice 100 at random orientations. Thus, on the basal plane 101, the vertical bonds extending upward from the three uppermost atoms of each oxygen hexagon may be three lone pair electron clouds, three hydrogen atoms, two lone pair orbitals and one hydrogen atom, or two hydrogen atoms and one lone pair orbital. From hexagon to hexagon, the distribution of vertical bonds can vary randomly. The IIDs discussed so far, with the exception of CHD/CHT motif IIDs, can bond only a fraction of the possible basal plane binding sites that are available due to this randomness of the basal plane bonding elements. This will tend to limit the maximum activity of the IID.

CHD and CHT Motif IIDS. Although "crinkle complementarity" can be retrospectively observed in IB2, IB3, and IB4, only the CHD/CHT motif of FIGS. 11A, 11B, and 11D and of FIGS. 12–15 combines "crinkle complementarity" with bonding that is capable of matching any encountered ice orbital distribution on the targeted ice crystal face or feature and with excellent orbital alignment ("steering"). Further, the commercial availability of CHD and CHT for use as reagents for polymer sythesis is another advantage of this motif.

Figure 16:
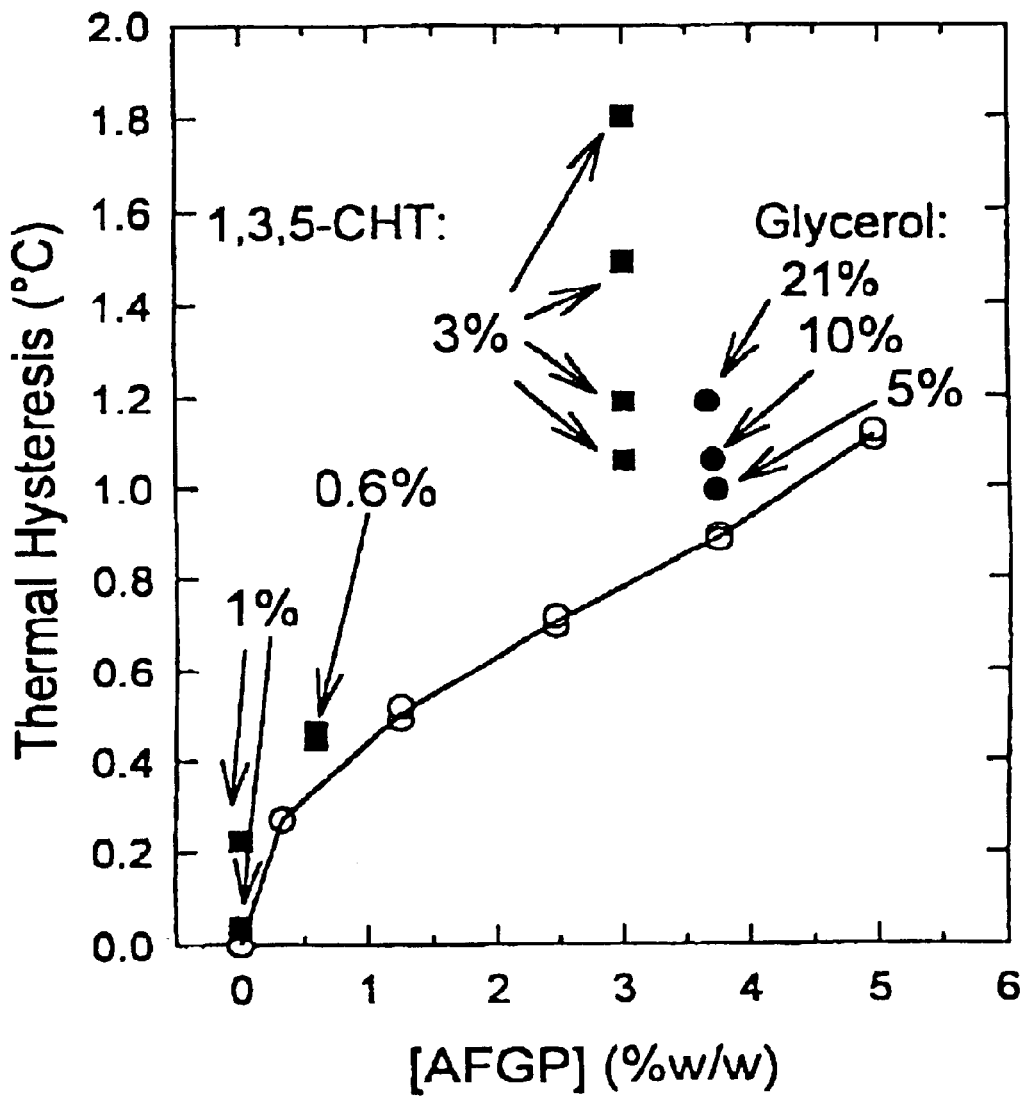
FIG. 16 is a graph showing effectiveness of CHT as an ice growth inhibitor.

FIG. 16 illustrates thermal hysteresis activity achieved by CHT with and without the simultaneous presence of fish antifreeze glycoprotein (AFGP). The figure also illustrates the effect of glycerol on thermal hysteresis activity of the AFGP. The figure illustrates the fact that, in the absence of AFGP, some thermal hysteresis activity was detected for 1% w/w CHT, an unprecedented observation for any small molecule. In addition, in combination with about 3% w/w AFGP, 3% w/w CHT produced an additive thermal hysteresis that was about equivalent to that produced by AFGP itself, and greater than that produced by combining AFGP with 20% w/w glycerol. Such effects by a small molecule ($M_r$ of CHD, 116 daltons) are wholly unprecedented and are beyond the imaginings of the prior art, and appear to constitute novel physical phenomena (new physics) that provide the "proof of principle" for wholly synthetic IIDs as described herein.

Figure 17A:
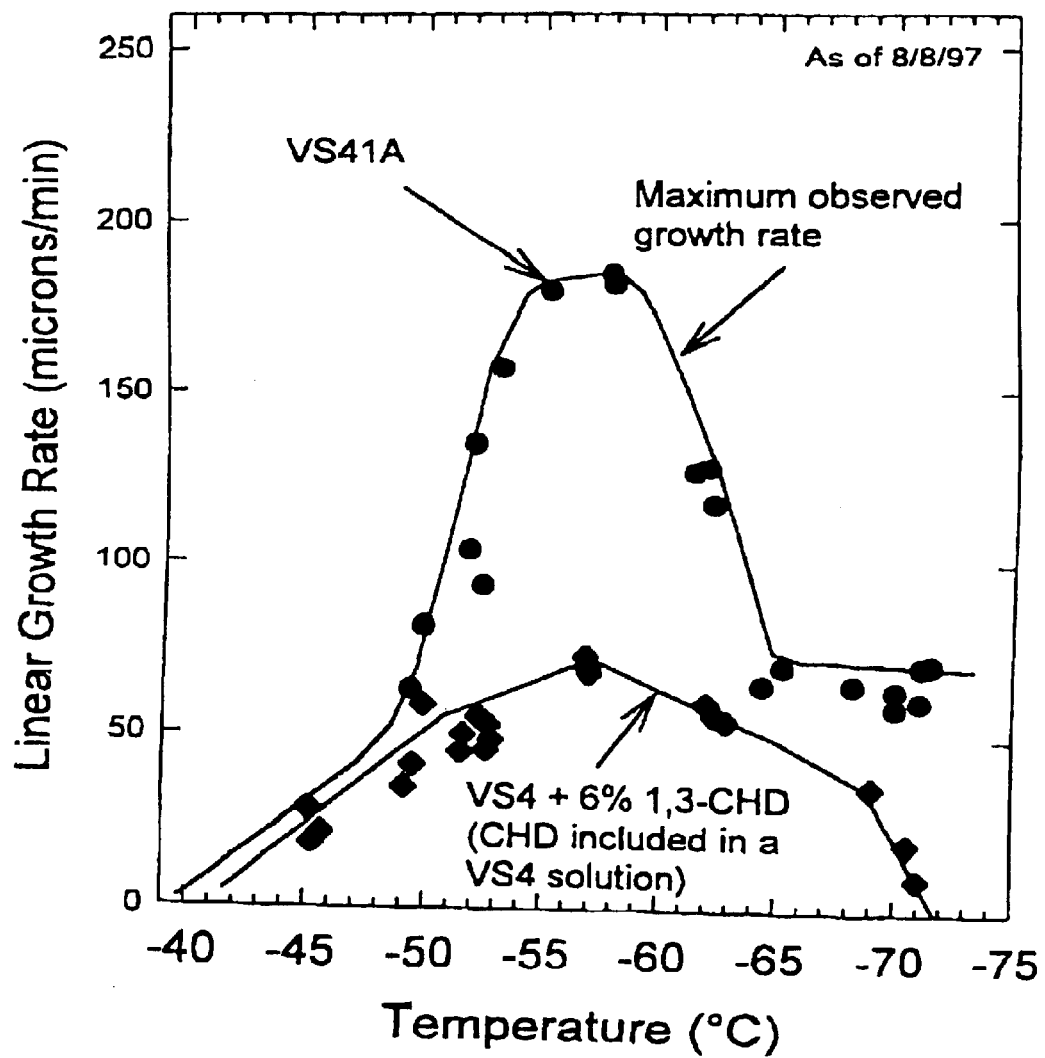
FIGS. 17A and 17B are graphs showing effectiveness of CHD as an ice growth inhibitor.
Figure 17B:
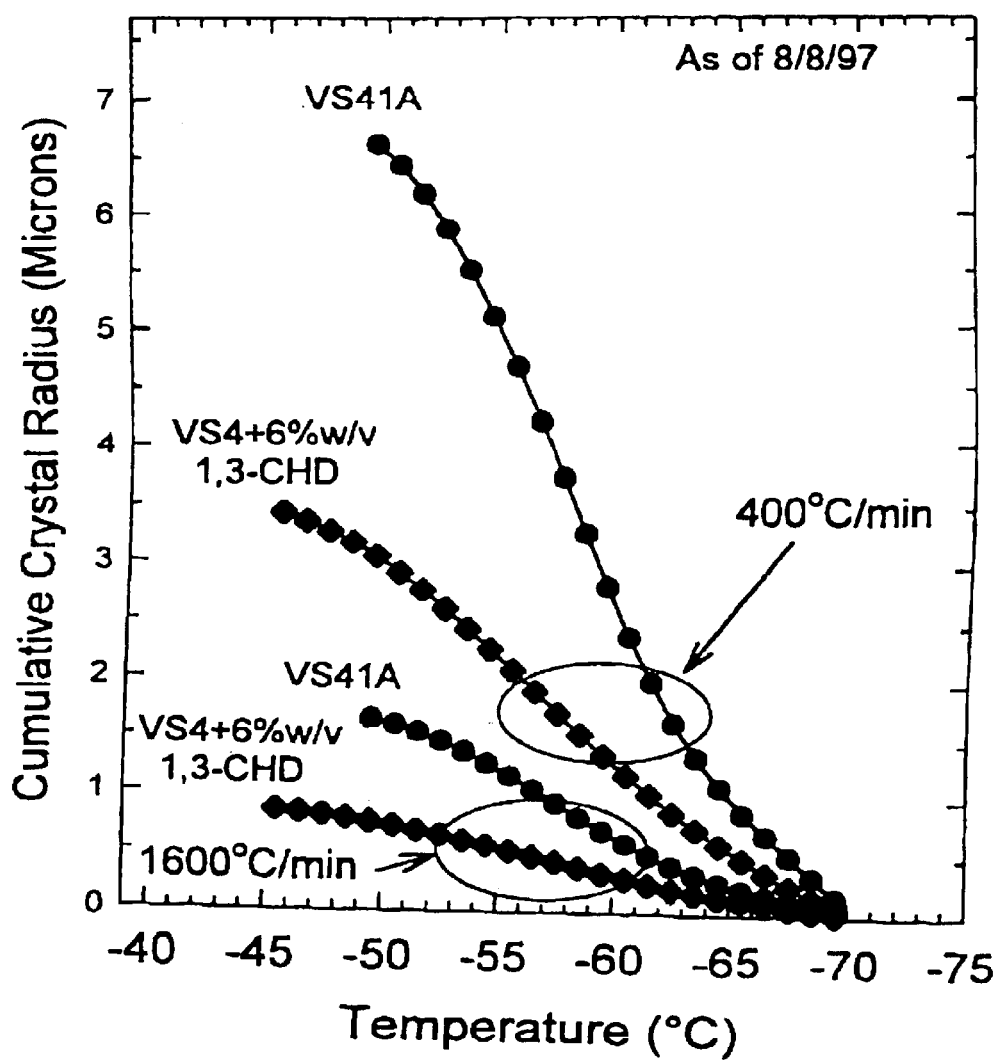

FIG. 17A illustrates data on ice crystal growth rates in a concentrated cryoprotectant formula (VS4, a 49% w/v solution whose composition was given above) containing 6% w/v CHD as a function of temperature. The data are compared to a similar formula (VS41A), in which the cryoprotective solutes are increased by $^{55}/_{49}$ths to form a 55% w/v solution devoid of CHD. VS41A is a low-toxicity vitrification solution currently being studied for the cryopreservation of rabbit kidneys by vitrification. FIG. 17A indicates that, by replacing a fraction of VS41A gram-for-gram with CHD, the growth rate of ice in the solution can be substantially diminished. FIG. 17B shows that this effect will make crystals that form at −70° C. during rapid warming (at 400 or at 1600° C./min) smaller by about a factor of two, which could greatly reduce biological injury during warming after previous vitrification.

Figure 18:
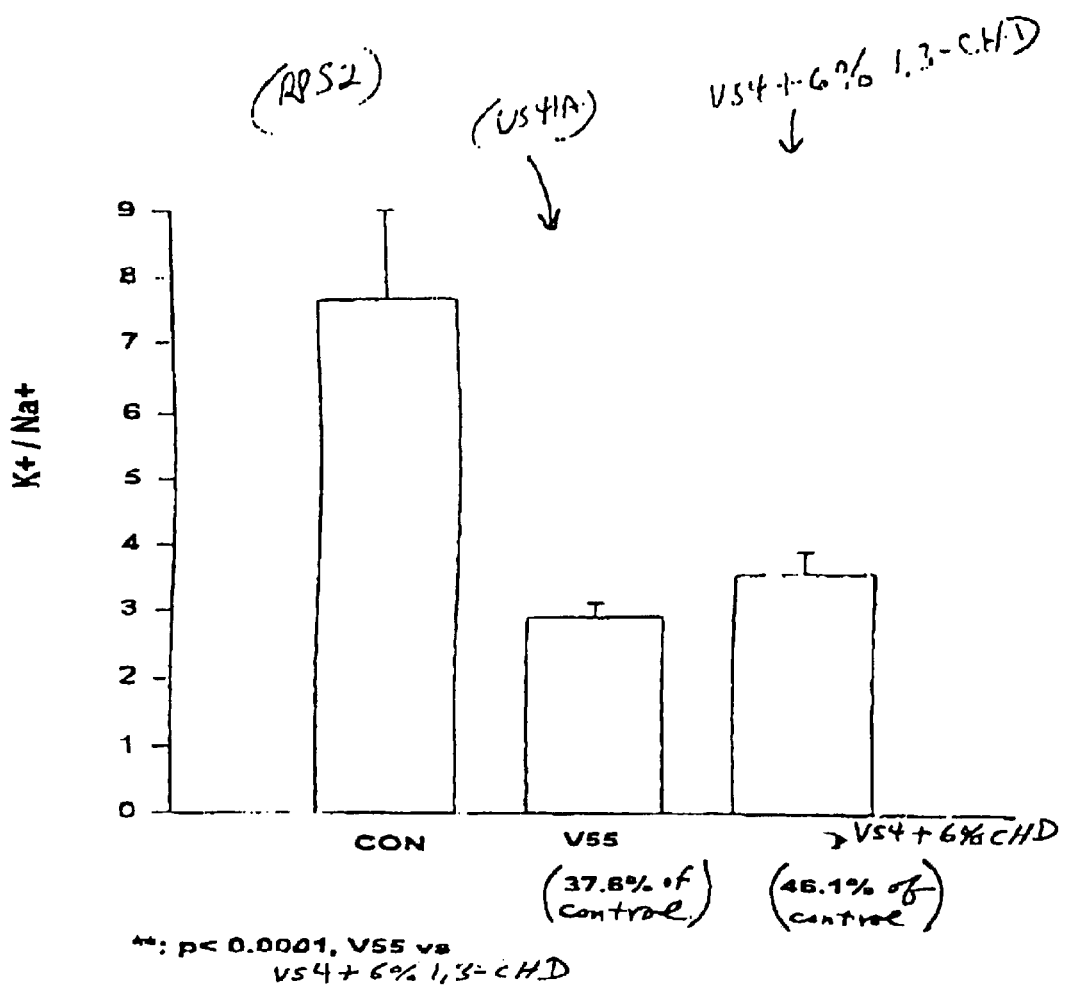
FIG. 18 is a graph showing the lack of toxicity of CHD in a vitrifiable concentration of cryoprotectant, relative to an equivalent quantity of cryoprotectant.

FIG. 18 illustrates data on the toxicity of VS4+6% w/v CHD vs. VS41A for rabbit renal cortical slices. The two formulae appear to be comparable in toxicity, and yet the CHD formula supports much less ice growth, as shown in FIG. 17A. Consequently, the CHD formula appears to be superior for cryopreservation in comparison to the VS41A. This is the first advance over VS41A since 1985.

In addition to these observations, 6% w/v CHD in water has been sprayed onto a test plant and exposed to the roots of a test plant growing in a natural setting in the summer, and it was determined that these modes of exposure to CHD did not result in any apparent negative effect on the plant, implying the utility of CHD for protecting crops from freezing in the winter.

The IIDs shown in FIGS. 7–9 show that "crinkle complementarity" can be attained in atoms incorporated into 5, 6, and 7-membered aliphatic carbon (or carbon-oxygen) rings, with and without the inclusion of a double bond in one such ring and with and without the inclusion of atoms that are externally attached to such rings. The most preferred IIDs shown in FIGS. 11–15 show that "crinkle complementarity" can also be attained for atoms that are exclusively attached externally to six-membered aliphatic carbon rings. FIG. 19 further illustrates that basic "crinkle complementarity" can be approximated in linear aliphatic carbon chains by attaching a bonding group (in this case, OH) to every fourth carbon atom with the proper stereospecificity.

Figure 19B:
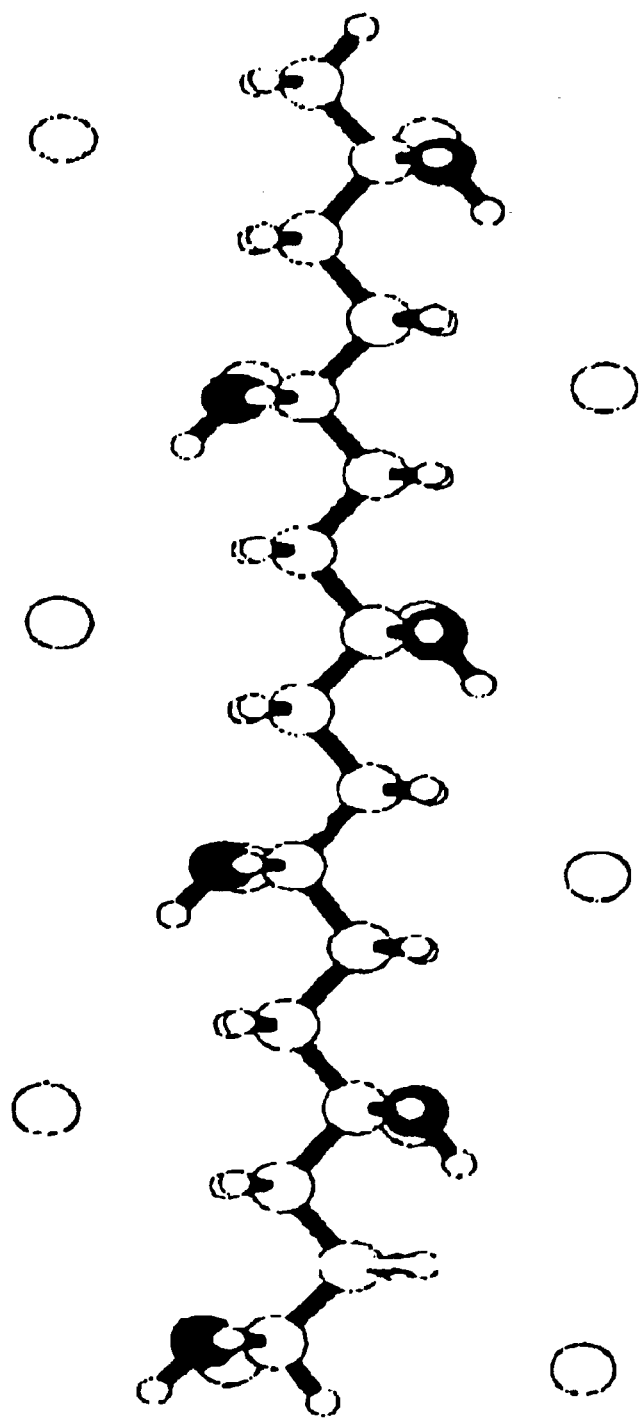

As shown in FIG. 19A, this arrangement provides oxygen spacings that match both the 4.5 and the 7.4 angstrom periodicities of the basal plane and, as shown in FIG. 19B, superimposition of this molecule on the pattern of bondable ice vertices on the basal plane can be done in such a way as to allow all available OH groups on the IID to associate with the available ice vertices. The orbital angular match between the IID and ice is not exact as in the case of the CHD or CHT motif, but is adequate for good IID activity. This IID is an excellent example of the "W" shaped ice bonding motif of FIG. 3.

The molecule of FIG. 19 is equivalent to molecule (1) (page 17), and is of the same essential motif as molecule (2) (page 17). Molecule (2) has been synthesized.

The examples given here are based on carbon, hydrogen and oxygen only and are with one exception devoid of bonds other than single bonds. Clearly, these restrictions are not necessary, but are selected for simplicity and to minimize biological toxicity.

Applications. The selection of specific IIDs will depend on the particular application at hand, and many applications of IIDs are envisaged.

By preventing Ostwald ripening, IIDs can, for example, prevent frozen foods such as frozen vegetables from sticking firmly together in the household freezer.

IIDs retard ice growth by physically blocking a fraction of the ice crystal surface and by effectively increasing the surface energy (increasing the evaporation rate) of ice near but not beneath the IID. The more area covered by the IID, the more ice surface will be available to participate in sublimation. Thus, paradoxically, use of an IID, which is often considered to increase ice surface energy (thus inhibiting crystal size increase) can also produce a net reduction in crystal sublimation rate (thus inhibiting crystal size decrease). Therefore, freezer burn in steaks and other products can be slowed, and slowed sublimation or melting of the polar ice caps in response to global warming could be attempted. For such uses, a non-toxic IID can simply be coated on the materials that are or are to be frozen.

By preventing coalescence of small ice particles in ice cream and similar products, the storage life of such products can be extended by months, and the ice cream itself will be somewhat softer at household freezer temperature than conventionally produced ice cream without using the enormous sugar concentrations required by the FreezeFlo process, for example. For this purpose, an effective amount of a non-toxic IID can be mixed with the product, preferably before packaging of the product.

By preventing seed crystals from nucleating supercooled water on crops such as citrus crops, millions of acres of agricultural products (e.g., all Florida orange groves) can be prevented from freezing on an annual basis, much more reliably and effectively than can be achieved via application of Frostban, a bacterium that simply lacks a nucleating site on its membrane. For this purpose, an IID which is preferably, but not necessarily, non-toxic can be coated on the crops, for example by spraying.

By slowing the growth of ice in vitrifiable solutions of cryoprotective agents, rare ice crystals will remain sufficiently small as to be innocuous to organs, body fluids and other body tissues or cells being vitrified for clinical transplantation or transfusion. For this purpose, an IID which is preferably, but not necessarily, transplantable or transfusable, is added to the tissues, for example by inclusion in a cryoprotective solution.

For preservation by freezing rather than by vitrification, IIDs can be prepared that will be unable to interact directly with nucleating agents, thus allowing a freezing process in which nucleating agents are used to catalyze the formation of large numbers of ice nuclei and the IIDs simultaneously prevent these nuclei from growing to damaging sizes. This will effectively change the physics of ice so as to permit complex systems to survive or to withstand freezing.

IIDs can also be prepared specifically to interact with nucleating substances and thus directly inactivate them to enhance supercooling. This will prevent freezing altogether in many critical applications.

IIDs can also be utilized to stabilize formed ice crystals. For example, they can be used in the snowmaking industry to stabilize previously formed snowflakes to attain a longer-lasting "powder" for skiers' enjoyment. In this application, IIDs can be sprayed onto snow flakes as they are created. This will prevent recrystallization (coalescence) and sublimation (causing shape change) of the snow flakes.

IIDs also have important applications in the prevention of or removal of now-troublesome icing of automobiles, aircraft, rocket boosters, and similar equipment, and in the removal or safe navigation of icing on roadways. They can be incorporated, for example, into the substance and/or treads of tires, shoes, and mountain-climbing aids so that cars, people and other objects will not slip but will instead actually stick to ice, reducing accidents and injuries due to icy conditions. In this application, weak ice bonding would be used to prevent ice from detaching from the underlying ice, thus fooling the ice-bonding surface. IIDs can coat thin layers of ice on airplane wings and automobile windshields, presenting a greasy surface that will not stick to additional ice, thereby allowing additional deposited ice to simply be wiped or pushed off or to fall off rather than to be chiseled or melted off.

In these different applications, the non-ice bonding surface of the IID will be modified for ease of assimilation into the substrate material during the manufacturing process, or to achieve goals of solubility, texture suitability or of toxicity limitation. Modifications to the non-ice bonding surface will depend on the substrate material and will be apparent to those skilled in the art. Changes in the ice-bonding surface will be made to extend or reduce the ice adhesion strength in a straightforward manner for the application at hand.

As noted, IIDs can retard ice growth, ice recrystallization, and ice sublimation, but IIDs with a high density of ice bonding sites such as CHT can also induce nucleation. Environmentally non-objectionable IIDs could replace cloud-seeding chemicals such as silver iodide, thus avoiding pollution of the environment with heavy metals (silver), substances that can affect thyroid function (iodine), or other objectionable materials. Preferably, finely-powdered nucleating IIDs would be sprayed broadly over the tops of supercooled clouds to induce crystallization and hence precipitation, or could be allowed to be swept upward from the ground on updrafts the way silver iodide cloud seeding has sometimes been attempted.

Nucleator IIDs coupled to biologically important molecules using methods similar or analogous to fluorescent or other current tagging methods can be detected by their ability to nucleate water, thus indirectly revealing the presence of the coupled molecule. The coupled IID thus serves as a probe for detecting the fate and presence of the tagged molecule, which itself can not be directly detected. For example, if one wants to know whether molecule A interacts with molecules B, C, or D, one can mix A with B, C, or D, rinse away unreacted A, and see if the remaining solution has a high freezing point. If it does, it means bound A is still present, which means it is bound to B, C, or D.

Ice nucleating bacterial cell walls (commercially known as SnowMax) are routinely used in the snowmaking industry to make snow for skiers' enjoyment. The weight of Snow-Max power required to make one ice nucleus is relatively high because the entire lyophilized bacterium is used as the powder. IIDs such as IIDs with the CHT motif could be prepared in greater mass to volume dilutions than SnowMax solutions, thus saving space and weight for the snowmaker.

While this invention has been described in conjunction with specific embodiments thereof, it is evident that many alternatives, modifications and variations will be apparent to those skilled in the art. Accordingly, the preferred embodiments of the invention as set forth herein are intended to be illustrative only, and not limiting. Various changes may be made without departing from the spirit and scope of the invention as defined in the following claims.

What is claimed is:

1. A method of inhibiting growth of ice crystals, comprising:

identifying a material requiring inhibition of growth of ice crystals, and applying to said material a plurality of molecules in an amount effective for inhibiting ice crystal growth on or in said material;

wherein said molecules are selected from the group consisting of $CH_3(CHOH(CH_2)_3)_nCH_3$, wherein n is 2 to 3,000,

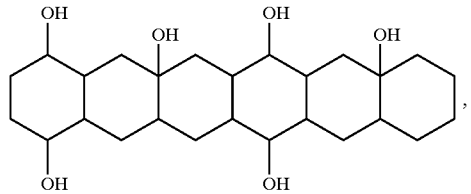

1,3-cyclohexanediol, cis,cis-1,3,5-cyclohexanetriol, $(CH_2OH)(CH_2)_3(CH_2OH)$ and $OH(CH_2)_3CHOH(CH_2)_2CHOHCH_2OH$, and wherein said material is selected from the group consisting of a vehicle surface, a road surface, a walkway, a light transmitter, and a utility line.

2. A method according to claim 1, wherein the molecules are 1,3-cyclohexanediol or cis,cis-1,3,5-cyclohexanetriol.

3. A method of inhibiting growth of ice crystals, comprising:

identifying a material requiring inhibition of growth of ice crystals, applying to said material a plurality of 1,3-cyclohexandiol molecules in an amount effective for inhibiting ice crystal growth on or in said material;

wherein said material comprises an organ that is to be cooled for cryopreservation; and cooling said material to a temperature at which ice crystals can form.

4. A method according to claim 3, wherein said 1,3-cyclohexanediol molecules are mixed with at least one additional cryoprotectant.

5. A method of successfully cryopreserving a material selected from the group consisting of an organ and tissues comprising applying to said material a plurality of molecules in an amount effective for inhibiting ice crystal growth on or in said material; wherein said molecules are 1,3-cyclohexanediol; and freezing the material having the plurality of molecules applied to cryopreserve the material.

* * * * *